United States Patent [19]

Ebner et al.

[11] Patent Number: 5,009,849
[45] Date of Patent: Apr. 23, 1991

[54] APPARATUS FOR CARRYING OUT CATALYZED CHEMICAL REACTIONS AND FOR STUDYING CATALYSIS

[75] Inventors: Jerry R. Ebner; John T. Gleaves, both of St. Louis, Mo.

[73] Assignee: Monsanto Company, St. Louis, Mo.

[21] Appl. No.: 372,095

[22] Filed: Jun. 28, 1989

Related U.S. Application Data

[63] Continuation of Ser. No. 923,890, Oct. 28, 1986, abandoned, which is a continuation-in-part of Ser. No. 682,028, Dec. 14, 1984, Pat. No. 4,626,412.

[51] Int. Cl.$^5$ .............................................. G01N 1/22
[52] U.S. Cl. ..................................... 422/83; 137/602; 137/625.4; 250/282; 250/288; 422/50; 422/80; 436/34
[58] Field of Search ................... 422/50, 80, 83, 198, 422/211, 213, 215, 100; 436/34, 36, 37; 250/282, 288; 251/129.01, 396; 137/560, 896, 802, 625, 625.4, 602

[56] References Cited

U.S. PATENT DOCUMENTS

| | | | |
|---|---|---|---|
| 2,281,527 | 9/1938 | Simpson et al. | 196/52 |
| 2,852,564 | 9/1958 | Warner et al. | 260/603 |
| 3,594,544 | 7/1971 | Wunderlich | 219/302 |
| 3,850,232 | 11/1974 | Wanka et al. | 165/107 |
| 3,861,878 | 1/1975 | De Corpo et al. | 422/50 |
| 3,907,707 | 9/1975 | Raffelson et al. | 252/437 |
| 3,909,202 | 9/1975 | Becker et al. | 422/80 |
| 3,992,109 | 11/1976 | Bock | 356/181 |
| 4,140,905 | 2/1979 | Polanyi | 250/282 |

(List continued on next page.)

FOREIGN PATENT DOCUMENTS

| | | |
|---|---|---|
| 1279008 | 7/1969 | Fed. Rep. of Germany . |
| 1542247 | 9/1970 | Fed. Rep. of Germany . |
| 2172147 | 9/1973 | France . |
| WO86/04276 | 7/1986 | PCT Int'l Appl. . |
| 1253984 | 11/1971 | United Kingdom . |

OTHER PUBLICATIONS

Jones et al., "J. Vac. Sci. Technol.", vol. 9, No. 6, pp. 1429-1441, Nov.-Dec. 1972.

(List continued on next page.)

Primary Examiner—Robert J. Warden
Assistant Examiner—Timothy M. McMahon
Attorney, Agent, or Firm—Senniger, Powers, Leavitt & Roedel

[57] ABSTRACT

Disclosed are an apparatus adapted for use in a temporal analysis of products (TAP) system for studying catalytic reactions, a catalytic reactor provided with heat exchange capability and useful in the TAP system, and an apparatus for use in gas processing which can also be used in a TAP system. The gas processing apparatus includes a manifold for introduction of a plurality of gases into a gas processing system. The manifold comprises a plurality of channels through which gas may flow toward the gas processing system, and a mixing chamber having an inlet in communication with the plurality of channels and an outlet in communication with the gas processing system. At least one of the channels has a rapidly operable feed valve at the terminus of the channel at which it communicates with the chamber inlet. The mixing chamber has a void volume that is small relative to the working volume of the gas processing system. The catalytic reactor comprises any of several novel combinations of catalytic reaction chamber and constructions providing for transfer of heat to the chamber. The novel TAP system apparatus includes a housing and, within the housing, a catalytic reactor, a collimating slit or the like for providing a resolved pulse of product gas, an analytical device for real time analysis of the product pulse, and circuitry for coordinating the product pulse with scanning of the analytical device. The TAP apparatus may also include a cryogenic surface surrounding the product pulse path, a low residence time mixing zone ahead of the reactor, and/or a manifold of the type described above.

21 Claims, 25 Drawing Sheets

U.S. PATENT DOCUMENTS

| | | | |
|---|---|---|---|
| 4,231,990 | 11/1980 | Jottier | 422/100 |
| 4,457,905 | 7/1984 | Ebner | 423/376 |
| 4,531,056 | 7/1985 | Labowsky et al. | 250/282 |
| 4,542,293 | 9/1985 | Fenn et al. | 250/288 |
| 4,568,831 | 2/1986 | Adams | 250/282 |
| 4,570,066 | 2/1986 | Schlag et al. | 250/288 |
| 4,626,412 | 12/1986 | Ebner et al. | 422/50 |
| 4,647,772 | 3/1987 | Lewis et al. | 250/282 |
| 4,682,026 | 7/1987 | Douglas | 250/282 |
| 4,740,152 | 4/1988 | Conrad et al. | 431/1 |

OTHER PUBLICATIONS

Merril, "Cat. Rev.", 4(1), pp. 115-159, 1970.
Jenkins et al., "J. of Physics", E vol. 6, pp. 827-832, 1973.
Fite, "Int. J. Mass Spec. and Ion Phy." vol. 16, pp. 109-124, 1975.
Pratt, "Cata.-Sci. and Technol.", vol. 80, chap. 4, pp. 173-226, Springer-Verlag, 1987.
Herz, "ACS Sym. Ser. 178 Cat Under Trans. Cond.", 1982.
Madix et al., "J. of Cat.", vol. 7, pp. 240-251, 1967.
Madix et al., "Surf. Sci.", vol. 20, pp. 377-400, 1970.
Hart et al., "Chem. Comm.", vol. 11, pp. 621-622, Jun. 1970.
Machiels, "ACS Sym. Ser. 178 Cat. Under Trans. Cond.", pp. 239-251, 1982.
Balzhinimaev et al., "React. Kinet. Catal. Lett.", vol. 25, Nos. 3-4, pp. 219-224, 1984.
Miyamoto et al., "J. Cat.", vol. 88, pp. 526-529, 1984.
Bernasek et al., "J. Chem. Phys.", vol. 62, Apr. 1975.
Palmer et al., "Cat. Rev.-Sci. Eng.", vol. 12(2), pp. 279-301, 1975.
Saltsburg, "Ann. Rev. Phys. Chem.", vol. 24, pp. 493-514, 1973.
Cardillo, "Ann. Rev. Phys. Chem.", vol. 32, pp. 331-357, 1981.
Bennett, "ACS Sym. Ser. 178 Cat. Under Trans. Cond.", 1982.
European Search Report, Examiner—Van Iddekinge.
Automatic Apparatus for Catalyst Characterization by Temp.—Programmed Reduction/Desorption/Oxidation, H. Boer et al.

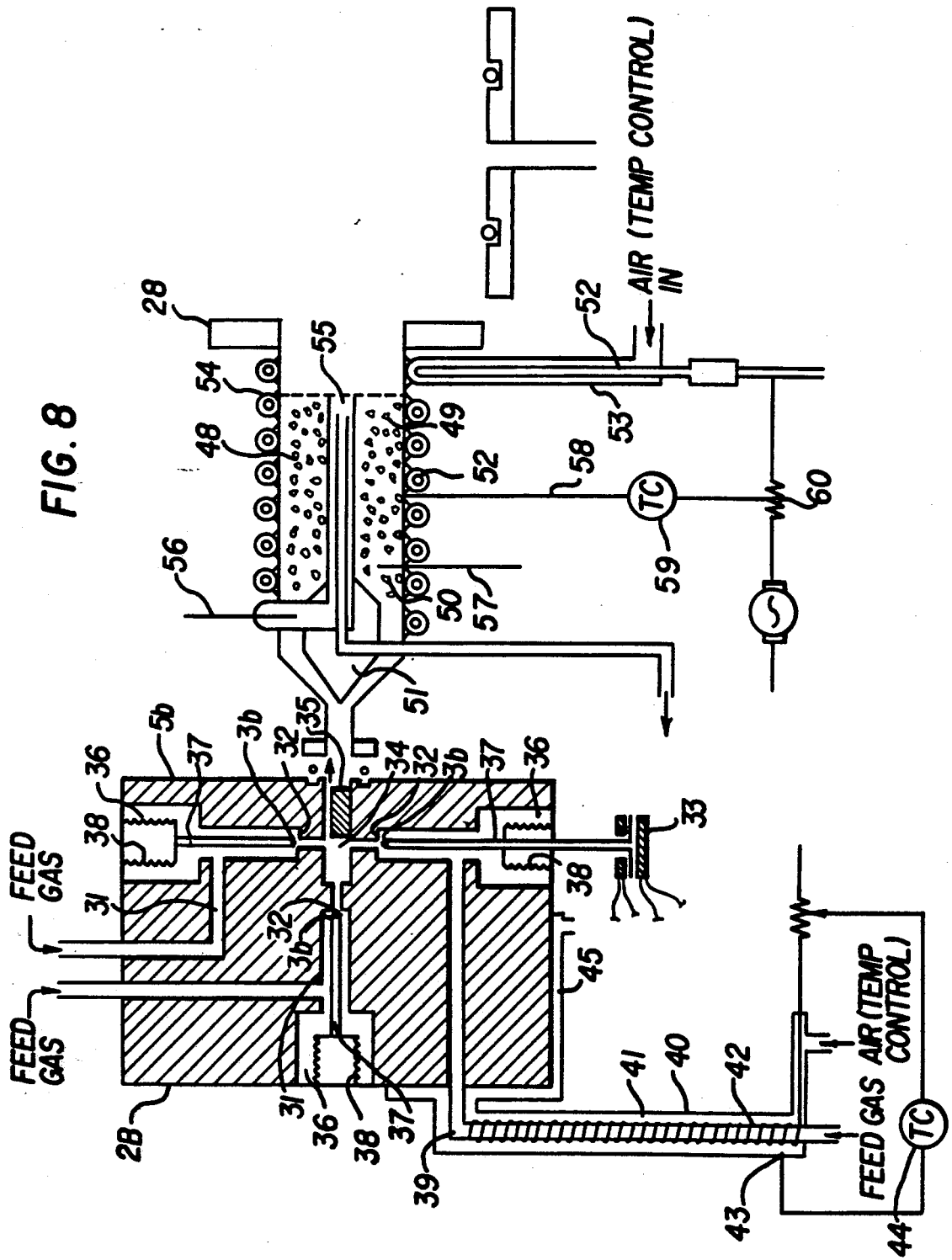

APPARATUS FOR CARRYING OUT CATALYZED CHEMICAL REACTIONS AND FOR STUDYING CATALYSIS

CROSS-REFERENCE TO RELATED APPLICATION

This is a continuation of application Ser. No. 923,890, filed on Oct. 28, 1986, now abandoned, which is a continuation-in-part of copending application Ser. No. 682,028, filed Dec. 14, 1984, now U.S. Pat. No. 4,626,412.

FIELD OF THE INVENTION

This invention relates to carrying out and studying of catalysis and catalyzed chemical reactions, particularly to heterogeneous catalysis.

BACKGROUND OF THE INVENTION

Catalyzed chemical reactions are widely used and are commercially very important. As a result, the development of new catalysts and catalyzed processes has been the object of a significant amount of technical development. The development of new catalysts and catalyzed reactions has been hampered by the difficulty encountered in obtaining basic information about the physical and chemical processes involved in catalytic activity and catalytic reactions, such as reaction intermediates, reaction mechanisms, adsorption and desorption of reactants and products in catalytic reactions, oxidation and reduction of catalysts, catalyst poisons, the concentration of reactants on a catalyst surface, and others.

Classically, this kind of basic information about the chemical and physical processes of catalysis has been deduced primarily from analysss of the final products of the reaction. Conclusions have been based on final products because of the difficulty in isolating and analyzing reaction intermediates, many of which are highly fragile and reactive species. Being able to determine directly the identity of these intermediates and to follow their production and consumption during the reaction would increase the understanding of catalysis and would facilitate the development of catalysts and catalytic processes.

One method that has been used to study the interaction of catalytic surfaces with reactant molecules is called molecular beam mass spectrometry. In this technique, a stream of molecules of reactant gas (a molecular beam) is directed at a target of the catalytic material, with the target oriented at an angle to the molecular beam. The molecules of the reactant gas strike the target, some of them react to form products and intermediates, and they rebound off the target in the direction of an aperture. A portion of the rebounding molecules pass through the aperture into the ionization chamber of a mass spectrometer, which analyzes the mixture for reactants, intermediates, and products. A variation on this molecular beam technique is called modulated molecular beam mass spectrometry, in which the initial molecular beam of reactant gas is modulated, such as with a rotating "chopper", to produce a series of pulses of the reactant gas. The result is that a series of pulses of gas enter the mass spectrometer for analysis.

In these molecular beam techniques, the entire assembly is enclosed and is operated in a vacuum. The vacuum is necessary to achieve the molecular flow to form the molecular beam, and is necessary for operation of the mass spectrometer.

The vacuum required, along with the fact that the molecules strike the catalyst target and rebound to the detector combine to make the number of reaction opportunities for each molecule of reactant very small. It has been estimated that the number of collisions between a given molecule of reactant gas and the target catalyst would be 10 or less, and that the number of collisions between a given molecule of reactant gas and other gas molecules would also be 10 or less. This means that these molecular beam techniques are practical only for highly reactive systems, in which sufficient reaction occurs in the small number of reaction opportunities to produce detectable amounts of products and intermediates. Most commercially important catalyzed reaction systems are not reactive enough for use with molecular beam techniques. The catalyst suitable for use with molecular beam techniques must be made into a target with a surface regular enough so that the direction of rebound of the reactant gas molecules can be directed toward the mass spectrometer. Not all catalysts can be formed into such a target.

Conventional techniques have been adapted to try to isolate and analyze for reaction intermediates. One common technique involves a reactor containing a catalyst, through which an inert carrier gas flows continuously. A pulse of reactant gas is injected into the carrier gas and is carried through the catalyst. As the product gas exits the reactor, samples are taken and analyzed. This type of system is normally operated at or near atmospheric pressure. The number of collisions between an average molecule of reactant gas and the catalyst is very high, and has been estimated to be far greater than $10^6$. Similarly, the number of collisions between an average molecule of reactant gas and other gas molecules has been estimated to be far greater than $10^6$. Due to the large number of reaction opportunities, the number of fragile and highly reactive intermediates that emerge from the catalyst is very small, and is usually too small to be detected.

The method and apparatus of this invention overcome some of the problems associated with prior art techniques to study catalysis. This invention preserves and detects fragile and highly reactive reaction intermediates of catalyzed chemical reactions, and preserves the time sequence of reactant/intermediate/product species evolved in a catalyzed chemical reaction. Practice of the novel process of the invention further requires provision of systems for delivery, temperature control and mixing of inlet gas, as well as reaction systems which can be operated under temperature control to produce a pulse of product gases that can be analyzed to provide meaningful information on the kinetics, reaction equilibria, and adsorption/desorption phenomena involved in the catalytic reaction.

A particular need exists for an apparatus operating under substantial vacuum which allows effective evaluation of catalytic reaction systems in which one or more of the feed materials has a relatively low vapor pressure at ambient temperature. For example, in studying the oxidation of butane to maleic anhydride, it may be desirable to feed maleic anhydride to the catalyst bed in order to investigate its decomposition over the catalyst. However, at room temperatures maleic anhydride has a vapor pressure of less than one torr, which is insufficient for such experiments. To circumvent and solve this problem, the vapor pressure of maleic anhydride or other low volatility feed materials may be raised by heating the maleic anhydride to elevated temperatures. This, however, poses special problems since not only the sample container must be heated but also all of the sample feed lines and the contacted valve parts must be heated. If they are not heated, the vapor will condense on the cooler surfaces.

SUMMARY OF THE INVENTION

One embodiment of this invention is an apparatus comprising:

a. an enclosed housing with a means for producing a substantial vacuum within said housing;
b. within said housing, a reactor having a zone defined in the reactor containing a reaction catalyst, the reactor being structured to allow a reactant gas to pass through said zone and to produce a product gas;
c. a means for introducing a rapid pulse of reactant gas to the reactor;
d. means for withdrawing from the reactor a pulse of product gas;
e. within said housing, a means for resolving said pulse of product gas to produce a resolved pulse of product gas in which the molecules of product gas are moving in substantially parallel paths;
f. means for providing real time analysis of said resolved pulse of product gas; and
g. a means for coordinating the actions of said rapid pulse introducing means and said analysis means so that scanning by the analysis means coincides with the arrival of a resolved pulse of product gas.

Another embodiment of this invention is a method, comprising:

a. introducing a very rapid pulse of a reactant gas to a catalyst zone in an enclosure under a substantial vacuum;
b. passing said reactant gas through said catalyst zone to produce a pulse of product gas;
c. resolving said pulse of product gas to produce a resolved pulse of product gas in which the molecules of the product gas pulse are moving in substantially parallel paths;
d. analyzing said resolved pulse of product gas in real time, and in coordination with said very rapid pulse of reactant gas.

The method of this invention will be referred to herein as temporal analysis of products, or TAP, and the apparatus will be referred to as a temporal analysis of products reaction system, or TAPRS.

The invention is further directed to TAPRS apparatus of the aforesaid type which further comprises a cryogenic surface surrounding the path taken by the product gas pulse as the gas pulse passes from the reactor to the analysis means.

The invention is also directed to an apparatus of the aforesaid type which further comprises a reactant gas mixing chamber upstream of the reaction zone with respect to the flow of reactant gas. The mixing chamber has a void volume that is small relative to the working volume of the reaction zone, so that the residence time of gas in the reaction zone is substantially longer than the residence time of gas in the mixing chamber.

Further included in the invention is an apparatus of the aforesaid type which comprises a manifold within the housing for introduction of a plurality of gas streams into the reactor. The manifold comprises a plurality of inlet channels through which gas may flow toward the reactor, at least one of the channels having a rapidly operable gas feed valve at its downstream terminus. The downstream termini of the channels are closely adjacent to each other. The manifold further comprises a gas mixing chamber downstream of the plurality of channels, the mixing chamber being in flow communication with the reactor and having a void volume that is small relative to the working volume of the reaction zone, so that the residence time of reactant gases in the chamber is short compared to the residence time in the reaction zone.

The invention is further directed to an apparatus of the aforesaid type, further comprising a manifold for introduction of a plurality of gas streams into the reactor, the manifold comprising a plurality of inlet channels through which gas may flow toward the reactor. At least one of the channels is in gas flow communication with an inlet conduit for delivery of a reactant gas stream to the manifold. A control conduit for flow of a temperature regulating fluid is in heat transfer communication with the reactant gas inlet conduit so that heat may be transferred between the regulating fluid and the reactant gas flowing in the inlet conduit. The control conduit contains therewithin an electrical heater for supplying heat to the reactant gas stream and the regulating fluid. Each of the channels has a rapidly operable gas feed valve at its downstream terminus, the downstream termini of the channels being closely adjacent to each other. A mixing chamber downstream of the plurality of channels is in gas flow communication with the reactor.

The invention is further directed to a catalytic reactor system comprising a reaction chamber having a reaction zone defined therewithin. The reaction zone contains a solid state catalyst for catalyzing the reaction of reactant materials supplied to the reactor in the gaseous phase. The system includes a fluid flow channel for a heat transfer fluid, means for transfer of heat to the contents of the chamber from a heat transfer fluid flowing in the channel, and an electrical heater within the heat transfer fluid flow channel for supplying heat to the heat transfer fluid.

The invention is also directed to a catalytic reactor system comprising a reaction chamber having a reaction zone defined therewithin, the reaction zone containing a solid state catalyst for catalyzing the reaction of reactant materials supplied to the reactor in the gaseous phase. The system includes an electrical heating element outside of the chamber for supplying heat to the contents of the chamber, a conduit for flow of a temperature regulating fluid, and means for transfer of heat between the contents of the chamber and the temperature regulating fluid.

Further included in the invention is a catalytic reactor system comprising a reaction chamber having a reaction zone defined therewithin, the reaction zone containing a solid state catalyst for catalyzing the reaction of reatant materials supplied to the reactor in the gaseous phase. The system includes an electrical heating element outside of the chamber for supplying heat to the contents of the chamber, a sleeve of high conductivity material surrounding the chamber between the heating element and the outside surface of the chamber, a conduit for flow of a temperature regulating fluid, and means for transfer of heat between the sleeve and the temperature regulating fluid in the conduit.

The invention is further directed to a manifold for introduction of a plurality of gas streams into a gas processing system. The manifold comprises a plurality of inlet channels through which gas may flow toward the system, each of the channels having a rapidly operable gas feed valve at its downstream terminus, the downstream termini of the channels being closely adjacent to each other. The manifold further comprises a gas mixing chamber downstream of the plurality of channels, the mixing chamber having a void volume that is small relative to the working volume of the gas processing system so that the residence time of the process gases in the chamber is short compared to the residence time in the gas processing system.

The invention is further directed to a manifold for introduction of a plurality of gas streams into a gas processing system, the manifold comprising a plurality of inlet channels through which gas may flow toward the system, at least one of the channels being in gas flow communication with an inlet conduit for delivery of a process gas stream to the manifold. A control conduit for flow of a temperature regulating fluid is in heat transfer communication with the process gas inlet conduit so that heat may be transfered between the regulating fluid and a process gas flowing in the inlet conduit. The control conduit contains therewithin an electrical heater for supplying heat to the process gas stream and the regulating fluid. Each of the aforesaid channels has a rapidly operable gas feed valve at its downstream terminus, the downstream termini of the channels being closely adjacent to each other. A mixing chamber is downstream of the plurality of channels.

The invention further includes a system for heating a flowing low pressure gas. The system comprises a conduit for the low pressure gas, a control conduit for flow of a temperature regulating fluid, the control conduit being in heat transfer communication with the low pressure gas inlet conduit so that heat may be transferred between the regulating fluid and the low pressure gas flowing in the inlet conduit. The control conduit contains therewithin an electrical heater for supplying heat to the low pressure gas and the regulating fluid.

The invention is further directed to a method comprising introducing a very rapid pulse of a first reactant gas to a catalyst zone in an enclosure under substantial vacuum. Within a very short interval after the introduction of the pulse of the first reactant gas, a pulse of a second reactant gas is introduced to the catalyst zone. The pulses of reactant gases are passed through the catalyst zone to produce a pulse of product gas. The pulse of product gas is resolved to produce a resolved pulse of product gas in which the molecules of product gas are moving in substantially parallel paths. The resolved pulse of product gas is repetitively analyzed in real time in coordination with the arrival of the resolved product pulse, thereby providing multiple analyses of a single product pulse as a function of time related to the passage of the gases of the reactant pulses through the catalyst zone.

In another of its aspects the invention is directed to a method of the aforesaid type in which the reactant gases are passed through a packed catalyst zone, the resolving means comprises an adjustable aperture, and analysis is effected with a mass spectrometer.

The invention is further directed to a method in which a series of very rapid pulses of a first reactant gas are introduced to a catalyst zone in an enclosure under a substantial vacuum. The catalyst in the zone contains a second reactant in a condensed state which may be transferred from the catalyst by reaction with the first reactant. The series of pulses is introduced at substantially regular time intervals, and the number of pulses in the series is sufficient for removal from the catalyst of a sufficient proportion of the second reactant to result in a quantifiable change in the composition of product gas obtained from the catalyst zone. Each of the pulses of the first reactant gas is passed through the catalyst zone to produce a pulse of product gas. Each of the pulses of product gases is resolved to produced a series of resolved pulses of product gas in which the molecules of product gas are moving in substantially parallel paths. Each of the resolved pulses is analyzed in real time and in coordination with the arrival of the resolved product pulse.

The invention is further directed to a method in which a very rapid pulse of a tracer gas and a very rapid pulse of a reactant gas are introduced to a catalyst zone in an enclosure under a substantial vacuum. The pulses of reactant gas and tracer gas are passed through the catalyst zone to produce a pulse of product gas and a pulse of tracer gas at the exit of the zone. The pulse of product gas and the pulse of exit tracer gas are resolved, the molecules of gas in each of the resolved pulses moving in substantially parallel paths. The resolved pulses of product gas and tracer gas are analyzed in real time, and in coordination with the arrival of the resolved product pulse and the resolved tracer gas pulse, respectively.

DISCUSSION OF THE INVENTION

TAP can be used with any reactant gas, or any other reactant that will exist as a gas under the vacuum and temperature of the TAPRS. In its preferred embodiments, the TAP system is particularly adapted for studying reaction systems, in which one or more products or reactants have a low vapor pressure under ambient conditions. The reactant gas can either be a single component or have multiple components. The reactant gas may also be mixed with an inert diluent. However, an inert diluent is often not necessary, and may, in the instance of certain diluents, make analysis of the products and intermediates more difficult.

If the reactant gas has more than one component or if a diluent is used, it is usually preferable to mix the gases prior to introduction of the reactant pulse to the catalyst zone. This can be accomplished in a number of ways, such as mixing in the storage feed tank, or by inclusion of a mixing zone, either prior to the pulsing mechanism or between the pulsing mechanism and the catalyst zone. The mixing zone can be a simple tubular segment or it may be a cone with the wide end corresponding to the diameter of the reactor, and the narrow end to the opening in the pulsing mechanism. It may contain baffles, be packed with inert solid particles with low surface area, such an sintered silica, silicon carbide, stainless steel, pyrex, and the like, or have some other means of creating mixing turbulence.

The reactant feed system also includes a means for generating a very rapid pulse of reactants. As used herein the phrase "very rapid pulse of reactant gas" means a discrete brief injection of reactant gas preferably lasting no longer than 10 milliseconds, more preferably no longer than 1 milliseconds, and most preferably not more than 0.5 milliseconds, although in some circumstances the pulse may last somewhat longer than 10 milliseconds. It is very difficult using normal techniques to get a pulse shorter than 5 microseconds. The time for the pulses are measured at the full width at half the maximum of the pulse curve. The very rapid pulse of reactant gas can be generated in a number of ways, including, but not limited to a "chopper", e.g. a rotating disc with one or more segments removed, rotating in the stream of reactant gas, or more preferably, a high speed gas pulsing valve. High speed valves suitable for this use are available commercially. Suitable high speed valves include modified miniature solenoid valves, piezoelectric valves, pulsed molecular beam valves, and any other valve that opens and closes sufficiently rapidly to produce a very rapid pulse of reactant gas.

The very rapid pulse of reactant gas may be a single pulse, or multiple pulses up to 500 pulses per second, and under some conditions even more pulses per second. It is preferred that the pressure of the reactant gas and the duration of the very rapid pulse be regulated so that each pulse contains $10^{10}$ to $10^{21}$ molecules per pulse, more preferably $10^{13}$–$10^{18}$ molecules per pulse.

Under some circumstances, it may be desirable to pulse two reactant gases separately, either simultaneously or at different times. For instance if two gases react under ambient conditions it would be desirable to pulse them separately to avoid premature reaction. Also, if one component of a reactant gas mixture moves through the catalyst zone very quickly, but participates in a later step in a multistep reaction, it may no longer be present in the catalyst zone at the time it is required in the reaction. In this situation, it may be desirable to introduce a pulse of this particular component at a somewhat later time than the other components, in order to accomplish this kind of plural pulsing, a plurality of pulsing means may be required.

Dual pulsing or plural pulsing experiments may also be useful in assessing reaction mechanisms. Thus, for example, if reactants A and B are known to react to produce C, alternate experiments can be run, in one of which a pulse of reactant B is introduced to the catalyst zone at a very short interval following the introduction of a pulse of reactant A, and in the other of which the sequence is reversed. The interval between individual reactant gas pulses may be varied widely in accordance with the kinetics of the reaction and the desorption characteristics of the reactants. After resolution, the product pulse produced in accordance with each of these techniques may b repetitively analyzed in real time to produce multiple analyses of the single product pulse as a function of time related to the passage of the gases of the reactant pulses through the catalyst zone. Thus, a profile of the pulse is obtained with respect to the composition of the product gas. If, for example, the generation of C is significantly more substantial when a pulse of B follows a pulse of A then it does when the sequence is reversed, it may indicate that gas phase B reacts with adsorbed A, but that adsorbed B does not tend to react with gas phase A.

In another form of time differentiated reactant flow, a single reactant such as A may be pulsed through a catalyst zone in which a second reactant B is already present in a condensed state, either adsorbed on the surface of the catalyst or chemically combined as part of the catalyst. In this method a series of very rapid pulses of the first reactant gas is introduced to the catalyst zone at substantially regular time intervals. Each of the resolved pulses of product gas is measured in real time and the results compared as a function of time. Pulsing is carried out for sufficient period that the number of pulses is effective for removing from the catalyst a sufficient proportion of the second reactant to result in a quantifiable change in the composition of the product gas obtained from the catalyst zone. From data of this type, it is possible to glean information relating to the nature, number, and activity of catalyst sites involved in a particular reaction. Where intermediates and by products are known and/or have been identified by TAP analysis, such intermediates and by products may be pulsed through a reactor in which an adsorbed species is already present. The resulting analysis may elucidate information on whether the same or different catalyst sites are involved in different stages of the reaction, and what effect reaction conditions may have on competitive reaction routes.

As indicated above, the method of the invention is effective for determining which reactants may participate in a reaction in, or be made available from, an adsorbed state, and which reactants in the gaseous state may react with adsorbed or nascent species to produce the desired products. Thus, a very substantial amount of information on reaction mechanisms, reaction kinetics, and phase equilibria may be obtained from the combined effect of plural pulsing experiments in which slightly separated reactant pulses produce a single product pulse, as compared to the results of experiments in which the catalyst is initially loaded with one reactant and an extended series of pulses of another reactant is passed through the catalyst zone.

There may also be some circumstances in which a continuous feed may be desirable, along with either singular or plural pulsing. For example, continuous feed of a component might be used to solve the problem discussed above, where the component has left the reactor prior to its being required in the reaction. Continuous feed also provides an alternative technique for investigating how a catalyst performs if a substance is adsorbed on the catalyst surface. This can be accomplished by continuously feeding the adsorbing substance prior to and during pulsing of the reactant gas. Other situations in which a continuous feed would be desirable would be known to one skilled in the art. Continuous feeding is most conveniently accomplished using a low pressure capillary feed system or a leak valve. The rate of continuous feed should not be so great as to increase the pressure, in the catalyst zone or elsewhere in the enclosure, beyond operable limits.

In order to accommodate this multiplicity of feeds, it is preferred that the mixing zone be connected to the reactor and adapted for attachment of these feed lines.

The reactor can be of a variety of shapes, but is preferably tubular in shape to hold the catalyst. The inlet end of the reactor is adapted to receive the very rapid pulse of reactant gas. This can normally be accomplished with a simple small tubular connection, or by direct connection to the mixing zone. It may be advantageous under some circumstances to include a baffle in the inlet to the reactor to avoid the presence of dead space. It is also preferred that the inlet be equipped with a means of retaining the catalyst in the reactor. However this retaining means must not unduly interfere with entry of the pulse of reactant gas. A screen is the preferred retaining means, more preferably a stainless steel screen.

The enclosure and reactor and its contents must be maintained under substantial vacuum during operation. As used herein, the phrase "substantial vacuum" means a background pressure no greater than $10^{-4}$ torr, preferably no greater than $10^{-6}$ torr. Higher pressures within this range are more common when using a continuous feed, and intermittent pressures may be slightly higher during a pulse. In order to accomplish this, the reactor is in an enclosure fitted with a means for attaining a substantial vacuum, such as a vacuum pump, including but not limited to oil diffusion pumps, turbomolecular pumps, ion pumps, and cryo pumps. Cryogenic traps and cryogenic surfaces can be used to assist in maintaining vacuum.

It is preferred that the catalyzed reaction be run at controlled temperature, so it is desired that there be some means of controlling the temperature of the reactor. This can be done by use of a jacket or coils for a temperature control fluid or by resistance heating. The temperature control means should be able to provide for isothermal operation or for operation with a controlled rising or falling temperature. It is preferred that the reactor and the temperature control means be able to operate over a wide temperature range, for instance from about 100° K. to about 900° K., or that separate reactors and/or separate temperature control means be fashioned to operate at a desired temperature.

The reactor may be constructed of stainless steel, ceramic, or other suitable materials. The catalyst zone is usually simply a cavity in the reactor and can be of any convenient size. It is preferred that the catalyst zone be cylindrical, with a diameter from about 0.2 cm to about 2.5 cm and with a length from about 0.5 cm to about 5 cm, although it may be larger or smaller to fit the circumstances.

The catalyst may be particles packed into the catalyst zone or may be coated on the inside surface of the catalyst zone.

In order to get a sufficient amount of void space to have proper gas movement through a packed catalyst zone, it is referred that the catalyst particles have a diameter from about 1% to about 20% of the diameter of the catalyst zone, or more preferably approximately 10% of the diameter of the catalyst zone. However, larger or smaller particles may be used in some circumstances.

The only requirements for the catalyst is that it must have a sufficiently low vapor pressure to survive in the vacuum in the enclosure, and that it can either be formed into particles of the correct size or coated onto such particles or coated on the inside surface of the reactor. The catalyst may be supported or unsupported, a solid, or even a liquid, if its vapor pressure is sufficiently low and if it can be coated onto an inert support, or the surface of the catalyst zone.

While the gas is moving through the catalyst zone, under the conditions outlined above, it has been estimated that, on the average, a given molecule of gas will collide with the surface of the catalyst from about 100 to about $10^6$ time and possibly more times for catalysts that are microporous solids, and will collide with other gas molecules about $10^3$ times, or less. If the catalyst is coated on the inside surface of the catalyst zone, the number of collisions with the catalyst will be near the low end of the range, if the catalyst zone is packed, the number of collisions with the catalyst will be somewhat higher in the range. A packed catalyst zone is preferred.

The number of collisions experienced can be controlled within these ranges, for instance by controlling the number of molecules of reactant gas in the pulse, by using larger or smaller particles of catalyst to change the amount of void space in the catalyst zone, by lengthening or shortening the length of the catalyst zone, by increasing or decreasing the diameter of the catalyst zone, or by other techniques. In this way, the amount of reaction can be controlled, so that sufficient intermediates and products are produced so they can be detected, and yet the amount of reaction is limited so that at least some of the fragile and highly reactive intermediates remain unreacted. The amount of reaction can also be controlled to some extent by controlling other parameters, such as temperature, duration of the pulse, etc.

As a result of this flexibility the number of collisions can be controlled so that a large enough number of collisions occur so that TAP can be used with a large number of commercially important catalysts and catalyzed reactions. At the same time, the number of collisions of the fragile and reactive intermediates can be limited so that a significant portion of them survive and can be detected and analyzed.

The reactor also has an outlet means, through which the product gas mixture that has moved through the catalyst and reacted, can exit. As used here, "product gas" or "product pulse" is considered to be the gas mixture made up of reactants, intermediates, and products that has moved through the catalyst zone. The product gas exits as a pulse. However, the product gas pulse is of substantially longer duration that the very rapid pulse of reactant gas.

The gas molecules will leave the outlet means via molecular flow, that is by traveling through the substantial vacuum of the enclosure with the same trajectories that the molecules have as they diffuse out of the catalyst zone. It is preferred that the outlet means not unduly interfere with this molecular flow. The outlet means should preferably have a restraining device to hold the catalyst in the catalyst zone, in similar fashion to the inlet means. A screen is preferred, with a stainless steel screen more preferred.

A portion of the molecularly flowing product pulse will be moving directly toward the detector, with other portions moving obliquely. The TAPRS has at least one aperture situated directly between the outlet means of the reactor and the detector, and preferably two or more collimated apertures. The aperture can either be fixed or adjustable. This aperture serves to block any molecules not moving in a substantially straight path from the reactor to the detector. In this way the aperture serves to resolve the pulse of product gas into a pulse in which the molecules are moving in substantially parallel paths toward the detector. The preferred type of aperture is slit or an iris, more preferably an adjustable slit or iris.

Resolution of the product gas pulse is important because the distribution curve of molecules of various types as they are distributed in time within a pulse is important information. If molecules can reach the detector through a circuitous route ricocheting off the walls of the enclosure, this distribution in time within the pulse could be masked.

The resolved product pulse then moves to the detection and analysis portion of TAPRS. It is important that the detection and analysis be done in real time. As use herein, the phrase "real time analysis" means that the detection and analysis occur while the pulse is in the enclosure. Delayed methods of analysis such as collecting samples for later analysis or chromatographic techniques, would not allow for analysis of the distribution curve of molecules in time within a pulse, and would also allow for further reaction of the fragile and reactive intermediates.

Examples of real time analyses include mass spectrometry and laser induced fluorescence, time resolved infrared or ultraviolet/visible light spectroscopy, and the like, with mass spectrometry being preferred, and with mass spectrometry using a quadrupole mass analyzer being especially preferred because it is compact and can easily be adapted to and fitted into the enclosure. The size and design of the quadrupole mass analyzer can be varied, in a manner known to one skilled in the art, depending upon the sensitivity and mass range desired. Because a quadrupole mass spectrometer is the preferred type of detector, the remainder of the discussion will focus on that type of detector. Similar considerations apply to other types of detection and analysis systems.

The ionization mechanism can be any suitable ionization known in mass spectrometry, with photoionization and electron impact ionization being preferred. However, it is preferred that fragmentation of molecules during ionization be minimized. The quadrupole can be oriented parallel to or perpendicular to the flow of the resolved product pulse. It is only required that the ionization chamber be in a substantially straight line with the reactor outlet and the aperture so that it is in the path of flow of the resolved product pulse. It is preferred that the quadrupole be perpendicular to the flow of the resolved product pulse, to avoid having nonionized species striking the detector.

The mass analyzer operates most efficiently at a pressure below about $10^{-6}$ torr and more preferably below about $10^{-8}$ torr. Because of the presence of the catalyst with a very large surface area and because of injection of the reactant gas and other gases and because of product gas rebounding from the area surrounding the aperture, it is difficult to reduce the pressure near the reactor to this low a level. For this reason, it is preferred that the sector surrounding the reactor and the sector surrounding the detector have separate vacuum systems to produce a differentially pumped high vacuum system. The aperture or slit is a convenient divider for separating the two vacuum sectors. If two collimated apertures or slits are used, the enclosure can be divided into three vacuum sectors, etc. The larger the number of vacuum sectors, the greater the differential in vacuum that can be attained between the reactor sector and the detector sector. It is also preferred that there be a means, such as a valve, for closing off the reactor sector from the remainder of the enclosure, so the reactor can be changed or serviced without breaking vacuum in the remainder of the enclosure.

The mass analyzer will normally scan the intensity variation of the specified mass within a particular pulse as a function of time. Various masses can be similarly analyzed to produce a complete profile or reaction products and intermediates for each pulse.

The action of the analysis means must be coordinated with the pulsing mechanism, so that the time periods over which the analysis means is scanning coincide with the arrival of a resolved pulse of product gas. This can be accomplished by a conventional electronic timing mechanism, known to those skilled in the art. A timing mechanism can either be set up to trigger both the pulsing mechanism and the analysis means or it can be set up to sense the action of the pulsing means and trigger the analysis means in response.

The signal from the mass analyzer can be processed by conventional electronic means. It is preferred that the results of several scans be averaged to arrive at composite results. This averaging will account for statistical variations that may occur among different pulses.

The masses which are observed by the mass analyzer indicate reactants and the products and intermediates produced in the catalyzed reaction. And, the intensity variation curve for each mass scanned, and how these curves compare with the theoretical distribution curves, or with curves of other masses, gives an indication of the sequence and timing with which the molecules or fragments were produced in the catalyzed reaction.

The sequence and timing of production of the intermediates and products gives information relating to such things as mechanisms and kinetics of the catalyzed reaction. Changes in the distribution curve that occur as temperature changes can give indications of a number of things, such as how mechanisms and catalyst activity change with temperature, and of the desorption activation energy. TAP is also quite sensitive to the effects of changes in surface conditions of the catalyst. Other conclusions that can be drawn from this type of data would be known to one skilled in the art.

In carrying out the TAP method of the invention, a tracer gas is preferably passed through the TAPRS either before or during the passage of reactant gas therethrough. Observations of the time of passage of tracer gas through the system, and the characteristics of the tracer gas peak as measured by the analytical means, provide a calibration of the system and highly useful information for interpretation of analytical data on the product gas. For example, the breadth of the tracer gas peak provides an indication of the number of collisions of gas stream molecules with the catalyst. Since the breadth of the peak for a reactant, product of reaction, or other species interactive with the catalyst reflects both number of collisions and effects of adsorption, a comparison of the breadth of an inert tracer gas peak with the peak for an interactive species provides an indication of the adsorption effects for the latter.

The number of collisions is a function of the length of the catalyst bed, catalyst particle size, and porosity of the catalyst particle. The tracer gas is normally passed through the TAPRS before the injection of reactant gas, but can also be introduced simultaneously. Although the use of an inert tracer gas simplifies data interpretation and is, thus, generally preferred, once the absorption characteristics of a particular reactant gas are known that gas may be used as a tracer gas.

Of the inert gases which may be used as a tracer gas, argon is preferred. Lighter gases, especially helium, may be disadvantageous since they move too rapidly through the system and have a tendency to sweep out reactants and other species involved in the reaction.

DESCRIPTION OF THE DRAWINGS

FIG. 8 is a schematic drawing illustrating a novel feed manifold and preferred reaction system for use in the TAPRS;

Corresponding reference characters indicate corresponding parts in several views of the drawings.

FIG. 1 represents a typical TAPRS, with an enclosure (1), containing a reactor (2), and a high speed valve (3), to create the very rapid pulse of reactant gas, with a feed line for the reactant gas (4). The valve is connected to a mixing zone (5) contained in a transition piece located between the valve and the reactor. The transition piece is also fitted with a feed line for continuous feed (6), which may be used if desired. A product pulse (7) leaves the reactor and passes through an opening in a cryogenic plate (8), and passes through two collimated, adjustable slits (9), to produce a resolved product pulse (10). The resolved product pulse enters the ionization chamber (11) of a quadrupole mass analyzer (12). The quadrupole mass analyzer scans the resolved product pulse for the mass designated in the mass spectrometer electronics (13). The signal from the quadrupole mass analyzer is processed in usual fashion by the mass spectrometer electronics, and is sent to the signal averager (14). The signal averager is regulated by a clock (15), connected to a pulse generator (16) that activates the valve causing injection of a pulse of reactant gas. The clock senses a pulse and activates the signal averager to receive a signal for designated period of time and to store it. Normally the signal averager stores the signals from a series of pulses and averages them to reduce noise. The averaged signal is fed to a computer (17). The computer can be used to simply run a plotter (18) to plot the results, or the computer can store the signal and compile signals for each of the masses studied, to plot them all together or the computer could be used to calculate things such as the time of the intensity peak for a particular mass, the median residence time, a time weighted median residence time, or other values based upon the curves. In this configuration, the enclosure is divided into three sectors, the reactor sector (19), an intermediate sector (20), and the analyzer sector (21), each of which is equipped with its own vacuum pump (22). Additionally, the intermediate sector has a liquid nitrogen trap (23) to assist in maintaining vacuum. This multiple sector arrangement is useful to allow the mass analyzer to operate in a higher vacuum than it is possible to attain in the reactor sector.

In order to obtain the most definitive information regarding the reaction mechanism, it is essential that the reactants be available on the catalyst surface at the same time, and that product gases move in rapid straight line molecular flow toward the detector without excessive gas to gas collisions. Operation in such manner helps to avoid the destruction of evanescent intermediates by decomposition or reaction with other species, and promotes the capture and identification of such intermediates by the detector. Accordingly, it is desirable for the reactant and product pulses to be as sharp as possible, and for any backmixing of the reactant and product gas flow stream to be minimized.

As indicated above, rapid operation of the product pulsing means and collimation of the product gas stream assist in promoting a sharp pulse and substantially simultaneous delivery of simultaneously generated reactant gases to the detector. Also important to the effective operation of the TAP system are the characteristics of the mixing zone for reactant gases, but here the considerations may be somewhat conflicting. Thus, to promote sharp reactant and product pulses, it is important to prevent axial backmixing either ahead of or in the catalyst zone. On the other hand, to provide a properly proportioned supply of reactant gases throughout the catalyst zone, it is also important that the reactant gases be distributed radially with respect to the path of flow through the reaction zone, and that the radial components of the reactant gas molecular flow vectors be randomized.

Figure 1:
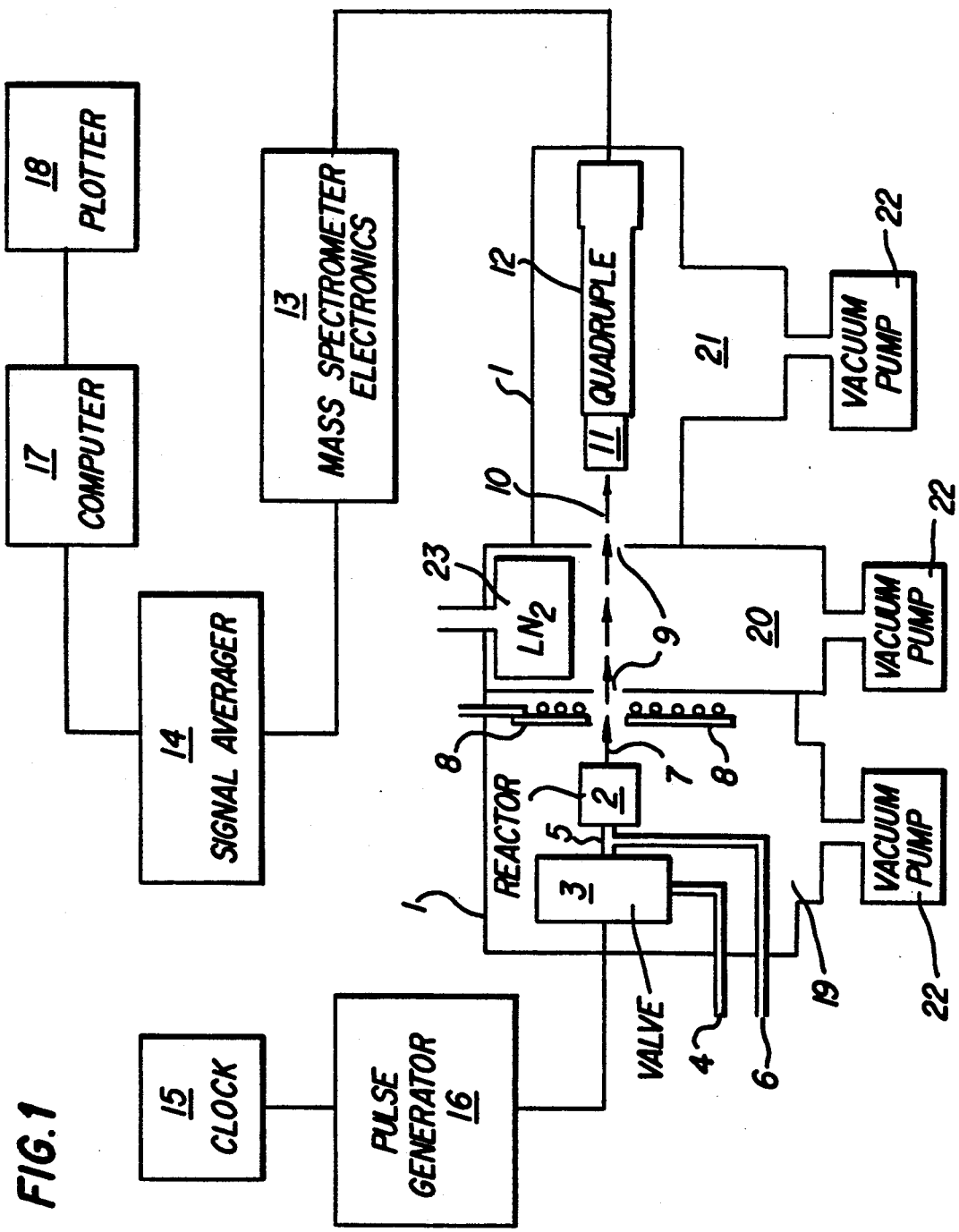
FIG. 1 is a schematic representation of a TAPRS.

In accordance with the invention, these needs are reconciled and accomplished by establishing a mixing zone whose volume is small relative to the working volume of the reaction zone, so that the residence time in the reaction zone is substantially longer than the residence time in the mixing zone, while further providing a baffle or other radial flow randomizing means upstream of the reaction zone. As illustrated in FIG. 1, the mixing zone is contained in a transition piece between the gas pulsing valve and the reactor. From that disclosure it will be understood, however, that the mixing zone further includes any dead volume in the reaction chamber upstream of the catalyst zone. Where a feed manifold is provided as described below, the mixing zone also includes the volume of the mixing chamber downstream of the gas feed valves inside the manifold. Whatever the components of the mixing zone, its volume is preferably minimized. More particularly, it is preferred that the volume of the mixing zone be no greater than about 1/10 the volume of the catalyst zone when empty.

Figure 6:
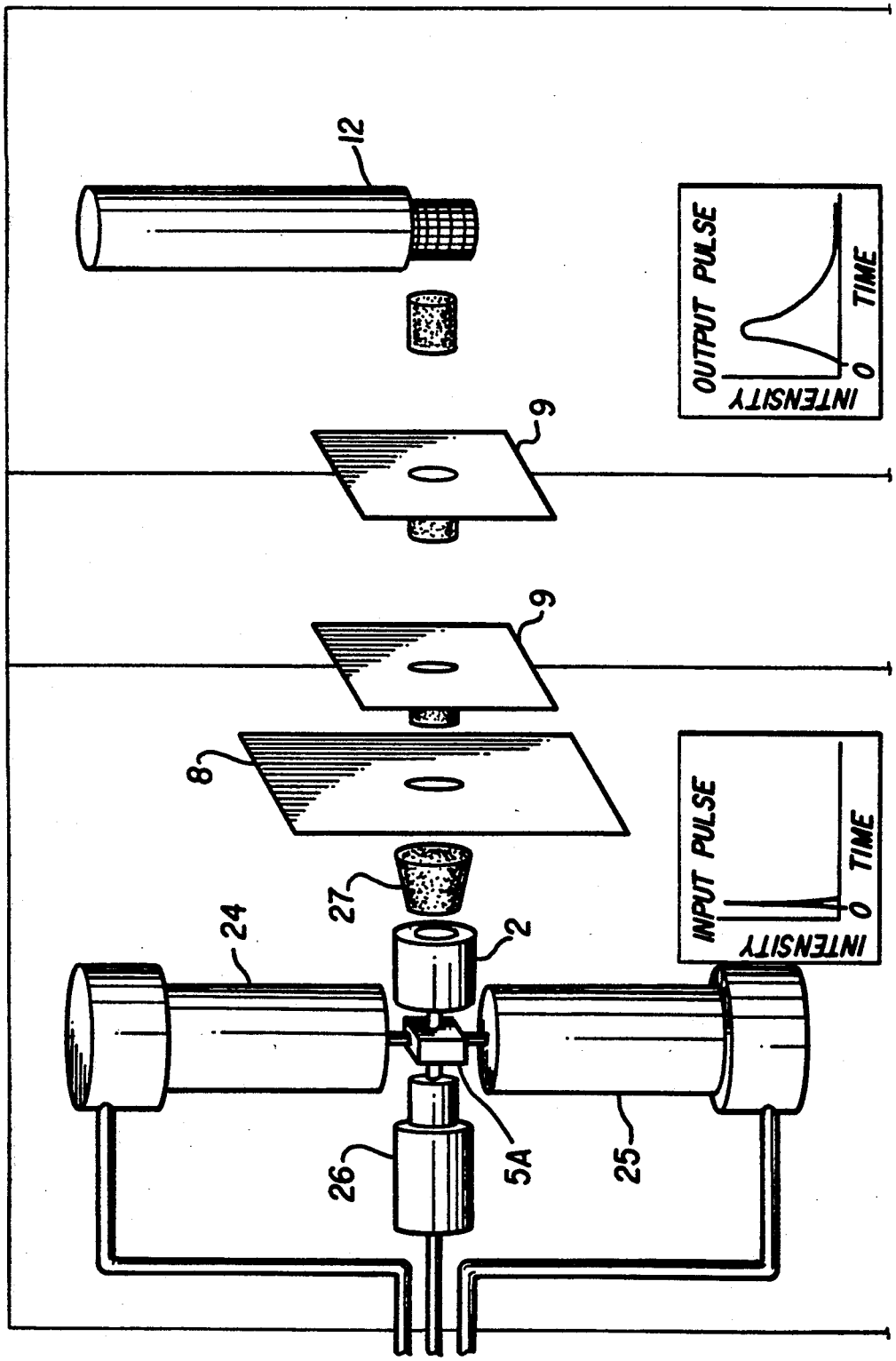
FIG. 6 is a schematic representation of a preferred embodiment of the TAPRS.

Illustrated in FIG. 6 is a preferred apparatus and process of the invention in which the feed gases are supplied through a "zero volume" manifold 5A. High speed valve operators 24, 25 and solenoid valve 26 control the supply of the reactant gases to the reactor through the zero volume manifold. The high speed valves control the flow of pulsed gases, while the solenoid is operated to provide continuous flow of a reactant or diluent gas. By "zero volume" is meant that the volume of the mixing chamber in the manifold downstream of the valves is small relative to the working volume of the reaction zone defined in the reactor 2.

As further illustrated in FIG. 6, the product gas pulse 27 leaving reactor 2 passes through cryogenic shield 8 and two collimating slits 9 before reaching quadrupole mass spectrometer 12. Through independent vacuum systems, the operating pressure in the reactor sector is maintained at about $10^{-7}$ torr, the intermediate sector between the collimating slits is maintained at about $10^{-8}$ torr, and the analytical sector is maintained at about $10^{-9}$ torr.

The cryogenic shield surrounding the product gas flow path serves to prevent stray molecules, which have initially failed to pass through the first collimating slit (or through the slit in the shield itself), from ricocheting off the housing walls and passing through to the detector at a time significantly later than the resolved pulse that contains molecules generated in the reactor at the same time as the ricocheted molecules. Such delay entry of ricocheting molecules into the detector would compromise the real time analysis and distort the results obtained from the TAP analysis.

Figure 7:
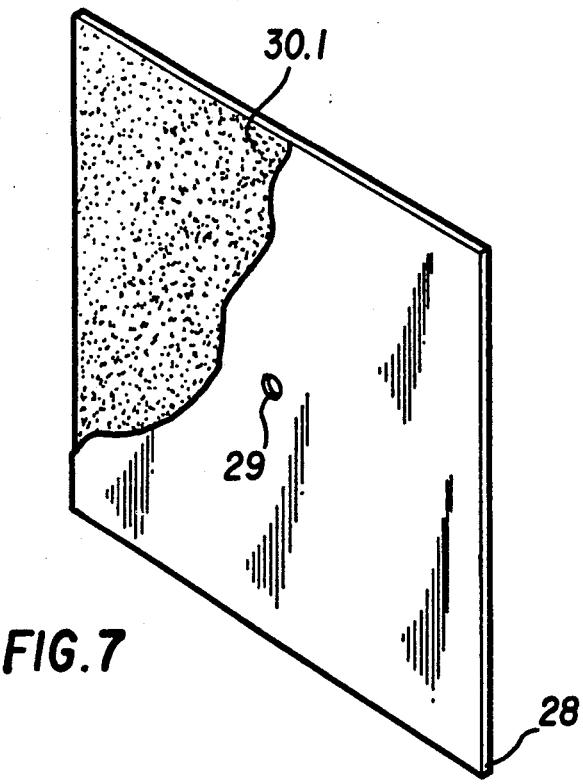
FIG. 7 and 7A is a detailed illustration of a cryogenic shield for use in the TAPRS.
Figure 7A:
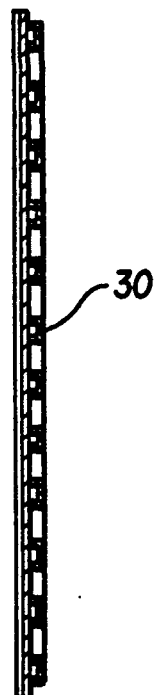

Detail of a preferred form of the cryogenic shield is shown in FIGS. 7 and 7A. This shield comprises a plate 28 of thermally conductive material having a central slit 29 therein for passage of the product gas pulse. A cryogenic conduit, comprising a coil 30, is affixed to a face of the disk to cool it and assure condensation of stray molecules which may strike the surface of the shield. A cryogenic liquid such as liquid nitrogen or liquid helium is passed through the coil. Optionally, the upstream face (or both faces) of the shield is coated with a molecular sieve material 30.1 which is effective for adsorbing gases that strike the shield, thus further aiding in the capture of such gases and thereby minimizing the number of stray molecules which may pass through the shield and distort the analysis of the product pulse. It will be understood that the cryogenic shield may have other configurations, for example, a tubular member through which the product gas stream passes. To assure that stray molecules are blocked irrespective of the angle from which they emanate, it is preferred that, whatever its geometric form or orientation of its surface to the direction of gas flow, the cryogenic shield completely surrounds the flow path of the product pulse.

Most preferably, a second cryogenic shield is provided, conveniently downstream of the second collimating slit. The presence of such a second shield affords maximum protection against passage of stray molecules to the detector means.

Slit 29 in the first cryogenic shield is preferably sized to have an acceptance angle essentially equal to that of the first collimating slit. If the slit 29 is sufficiently large to afford a wider acceptance angle, some molecules passing through it will rebound off the first collimating slit. Though this is not desirable, the cold surface presented by the shield normally will collect such stray molecules before they have a chance to ricochet through the collimating slit. If slit 29 is slightly too small, i.e., has an acceptance angle narrower than the first collimating slit, it will not adversely affect the resolution, but will reduce to some extent the number of molecules available for analysis at the detector means. Generally the slits in the first cryogenic shield, the first and second collimating slits, and the slit in the second cryogenic shield are adjusted to progressively increased size so as to maintain the same acceptance angle throughout. This assures the maximum product gas sample size without adverse effect on the resolution.

Important to the operation of the TAP system are control of the temperature of the reaction zone and of the inlet gases to the system. Control of reaction temperature is important, of course, to provide accurate determination of reaction mechanisms, reaction kinetics, and both reaction and adsorption equilibria, as a function of temperature. Control of reactant gas temperature is important not only as an adjunct to reaction temperature control, but also to allow the introduction of reactant materials that exist in a condensed state at normal temperatures and pressures. Many commercially significant gas phase, solid catalyzed, catalytic reactions fall in this category.

Illustrated in FIG. 8 is a preferred system which includes a feed manifold for introduction of reactant gases and a reactor which is adapted for effective temperature control. The manifold 5b comprises a block of metal having plurality of inlet channels 31 contained therein. Typically, the inlet channels may be provided by drilling the block. At the downstream terminus 32 of each inlet channel 31 is a valve 3b which is rapidly operable by a valve operator 33. A mixing chamber 34 is located downstream of the inlet channels. The mixing chamber is preferably provided by drilling a recess in a wall of the metal block at a point that is in common communication with the inlet channels. A rod 35 inside the mixing chamber serves to render its void volume very low.

The metal block is provided with apertures 36 to accommodate valve stems 37 which connect valves 3b to valve operators 33 located outside the block. Each of apertures 36 is closed with a bellows 38, and valve stem 37 extends through and is fixedly sealed, for example by a weld bead or solder, to the bellows that closes the aperture. Thus, the valve stem may be moved by the operator in opening and closing the valve without any disturbance of the seal that prevents ingress and egress of fluids to or from the manifold.

Particularly to provide for feeding of gases which have a low vapor pressure at room temperature, at least one of the inlet channels is in gas flow communication with a heated inlet conduit 39 for delivery of a reactant gas stream to the manifold. In operation of the TAPRS system, the reactant gas flowing in the inlet conduit may generally be at a pressure ranging from 5 torr to 2 atmospheres, or even higher, but is typically at a pressure in the range of 25–50 torr. Inlet conduit 39 is located within and concentrically aligned with an inlet assembly containment pipe 40, the annular space between the outside wall of conduit 39 and and the inside wall of pipe 40 defining a control conduit 41 through which a temperature regulating fluid, typically a gas such as air, is passed. Conduit 41 also contains an electrical heater 42 for supplying heat to the process gas stream and the regulating fluid. Via the heat supplied by heater 42, the process gas passing through conduit 39 is maintained in the vapor state. As a result of the heat transfer communication between process gas inlet conduit 39 and control conduit 41, the regulating fluid contained in the control conduit provides heat capacity for supplying heat to the process gas at points which might otherwise constitute cold spots that would promote condensation. The regulating fluid may also absorb any excess heat from the electrical heater, and thereby prevent the development of any hot spots at which the process gas might otherwise be caused to degrade. Both the temperature of the regulating gas and that of the process gas are readily controlled by a control system comprising a temperature sensor 43 positioned in control conduit 41 and a controller 44, responsive to sensor 43, which controls the flow of power to electrical heater 42. It has been found that the temperature of the process gas very rapidly and closely adjusts to the temperature of the regulating fluid.

Figure 9:
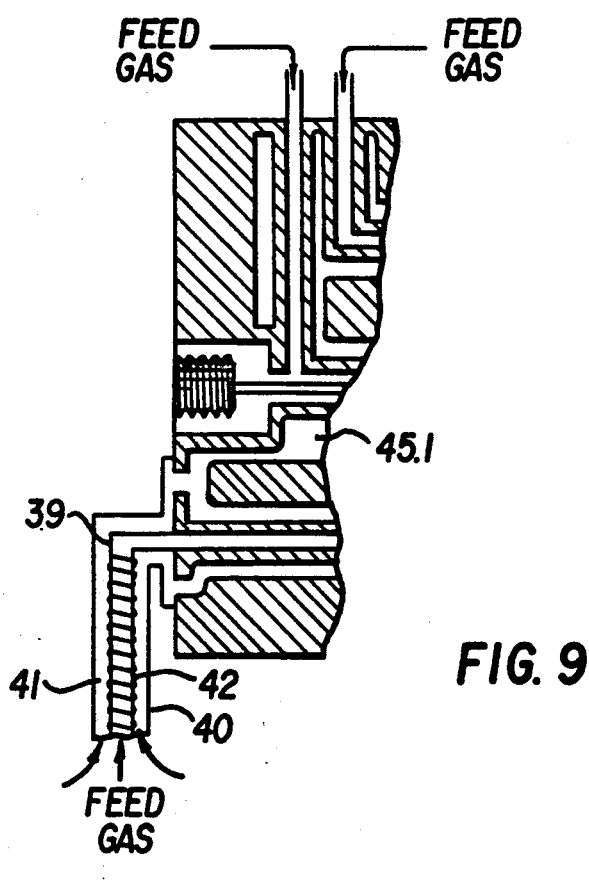
FIG. 9 is a detailed view illustrating an alternative means for heating the metal block of the feed manifold.

The temperature regulating fluid may also be utilized to heat the manifold itself and maintain it at an even constant temperature. As illustrated in FIG. 8, a jacket 45 on the outside of the metal block, in fluid flow communication with control conduit 41, comprises means for transfer of heat from the regulating fluid to the manifold. Alternatively, as illustrated in FIG. 9, the regulating fluid may be passed through a cavity 45.1 within the block to supply heat to the manifold.

Figure 10:
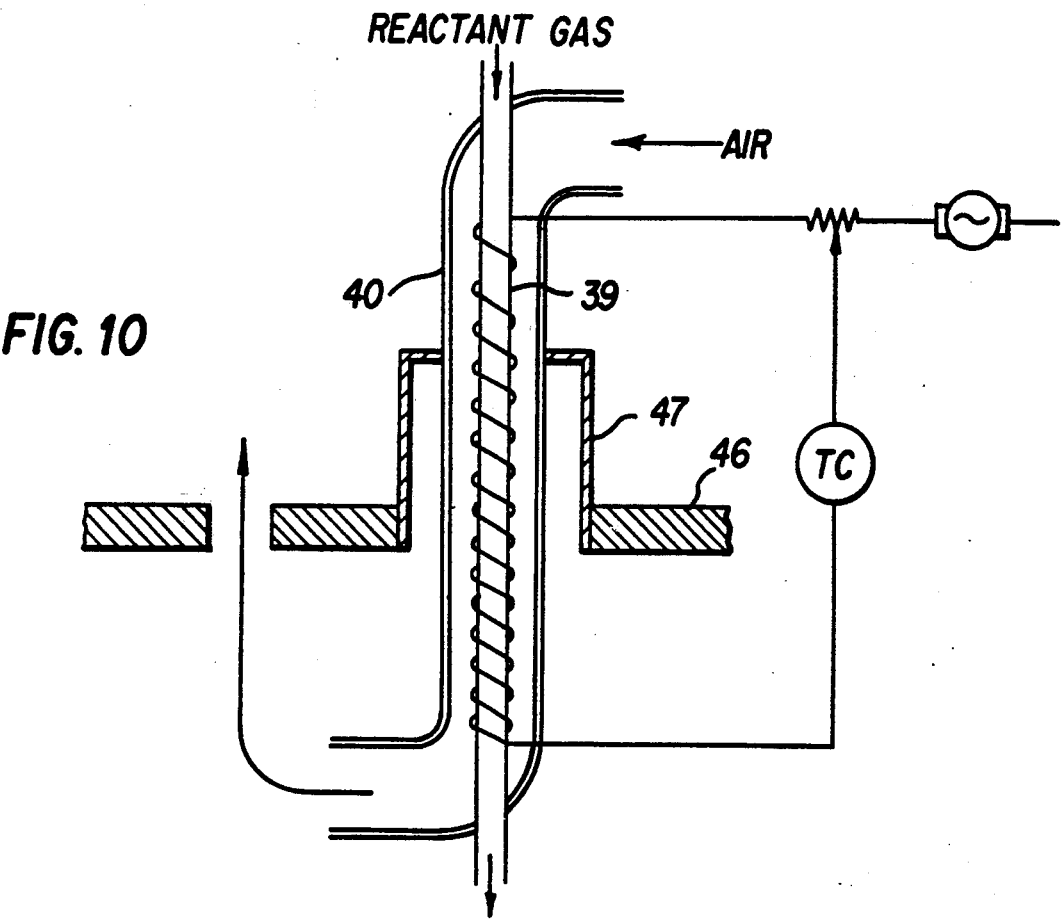
FIG. 10 is a detailed view showing a preferred system for connection of a feed gas inlet conduit and temperature control conduit to the feed manifold of the FIG. 8.

FIG. 10 shows a preferred system for connection of the inlet conduit and control conduit to the manifold. As there illustrated, inlet assembly pipe 40, containing inlet conduit 39, extends into the metal block through an opening in a flange 46 mounted on the block. The dimensions of the opening and location of the control conduit are such as to provide an insulating gap between the control conduit and the flange. A cap 47 is welded at its open (inner) end to the inside rim or face of the flange, and at its closed (outer) end to the exterior of the control conduit, i.e., the assembly pipe, thereby providing a sealed connection with a minimum path for heat loss from the inlet assembly to the mass of the flange and metal block.

Returning to FIG. 8, the preferred system there shown further includes a reactor 2b comprising a tubular reaction chamber 48 containing a catalytic reaction zone 49 packed with a particulate solid catalyst. Upstream of the reaction zone is a reactor mixing chamber containing inert particulate packing 50 and a conical baffle 51, the axis of the cone being substantially coincident with the gas flow axis of the reaction chamber so that the reactant gas passes around the periphery of the cone and then through the inert packing into the reaction zone.

In combination, the mixing chamber 34 of the feed manifold and the reactor mixing chamber, containing inert packing 50 and baffle 51, constitute the mixing zone for the TAP system of FIG. 8. Preferably, the void volume of both mixing chambers, and of the overall mixing zone, is small relative to the working volume of the catalytic reaction zone so that the residence time in the mixing zone is small relative to the residence time in the reaction zone. As indicated in the drawing, the downstream termini of the inlet channels are closely adjacent each other. This, and the presence of rod 35, contribute to minimizing the volume of the manifold mixing chamber 34, and thus of the overall mixing zone.

Heating of the reactor is afforded by the combination of an electrical heater 52 and a heat transfer fluid flowing outside the chamber which is heated by the electrical heater. A flow channel 53 for the heat transfer fluid includes a coil of tubing 54 surrounding the chamber 35 and in contact with the outside surface of the chamber, the contiguous wall portions of the coil and chamber comprising means for transferring heat to the contents of the chamber from the heat transfer fluid. Electrical heater 52 is located within the flow channel 53 and, as shown in FIG. 8, comprises a resistance wire disposed within coil 54 and substantially axially oriented within the coil. In this embodiment of the invention, the electrical heater is thus disposed adjacent the wall portions of coil and chamber which comprise the aforesaid heat transfer means, and heat may be supplied to the reactor both by conduction through those wall portions and by radiation from the resistance wire to the contents of the chamber.

As further illustrated in FIG. 8, the preferred reactor heating system further comprises means internal to the reaction chamber through which additional heat may be supplied to the contents of the reactor. Such means includes a tube or other heat transfer fluid conduit 55 contained within the chamber and in fluid flow communication with coil 54. Thus, heat transfer fluid passing through the coil, which is heated by electrical heater 52, also passes through conduit 55 and contributes further heat to the contents of the reactor.

Sensors 56, 57, and 58 are provided for respectively measuring the temperature $T_1$ in the heat transfer fluid channel downstream of the coil 54, $T_2$ in the gas stream upstream of the reaction zone, and $T_3$ in the reaction zone. Control of the temperature inside the reactor is preferably effected by feeding $T_3$ to a controller 59 and controlling the flow of power to the electrical heater, for example, by means of a rheostat 60, to maintain the desired value. Alternatively, reaction temperature can be controlled by controlling $T_1$. Adjustment of heat transfer fluid flow may also affect the temperature inside the reactor, but this flow is preferably set at a constant level, and control effected by regulating the supply of power to the electrical heating element.

Use of the reactor heating and temperature control system of FIG. 8 permits rapid heating of the catalyst bed inside the reactor. This in turn allows use of the system for such experimental techniques as temperature programmed desorption and differential thermal analysis. In carrying out such techniques, a reactant or other material is allowed to condense on the catalyst surface, and thereafter the catalyst is heated very rapidly. In a temperature programmed desorption, this method generates data indicative of desorption characteristics. In differential thermal analysis, the temperature is monitored during the course of rapid heating to determine the extent of heat generation relative to the heat input to the system. This in turn gives an indication of thermal stability of the species tested. In conjunction with operation of the mass spectrometer in the analysis sector, it may also give significant and useful data on reaction mechanisms, data that might not be determinable from a TAP analysis generated by feeding all reactants to the system.

Figure 11:
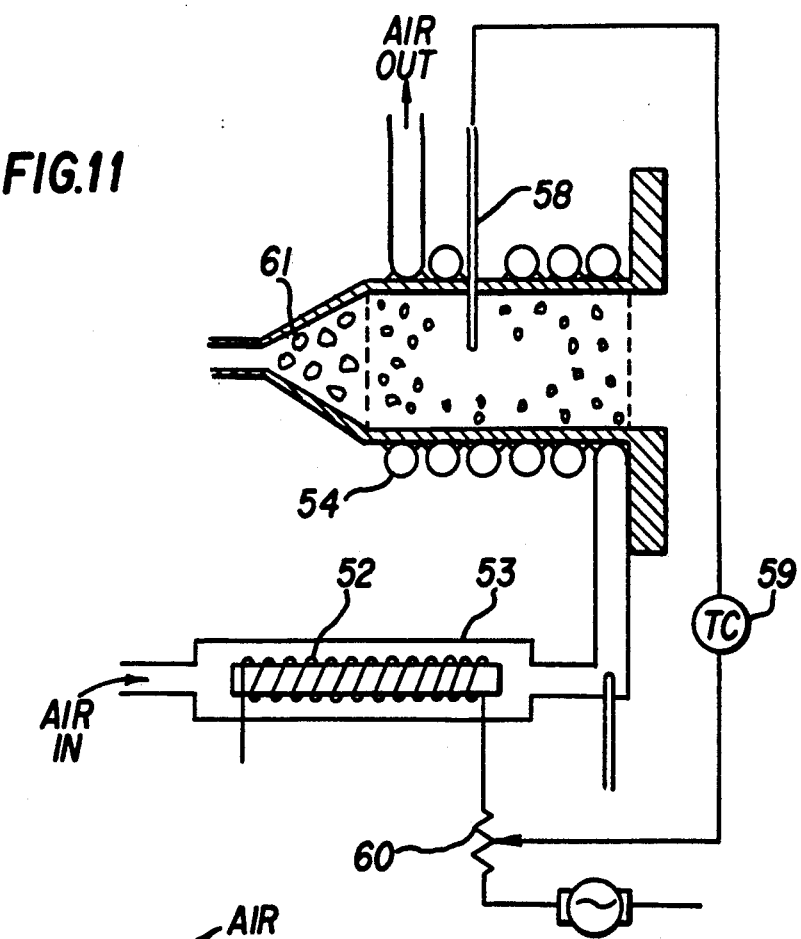

FIG. 11 illustrates an alternative embodiment of the reaction system in which the baffling means comprises quartz chips 61 in the inlet end of the reaction chamber. Also, in this embodiment, the heating element is contained within the heat transfer fluid flow channel 53 at a location remote from the coil 54. Otherwise, the system of FIG. 11 is generally similar to that of FIG. 8.

Figure 12:
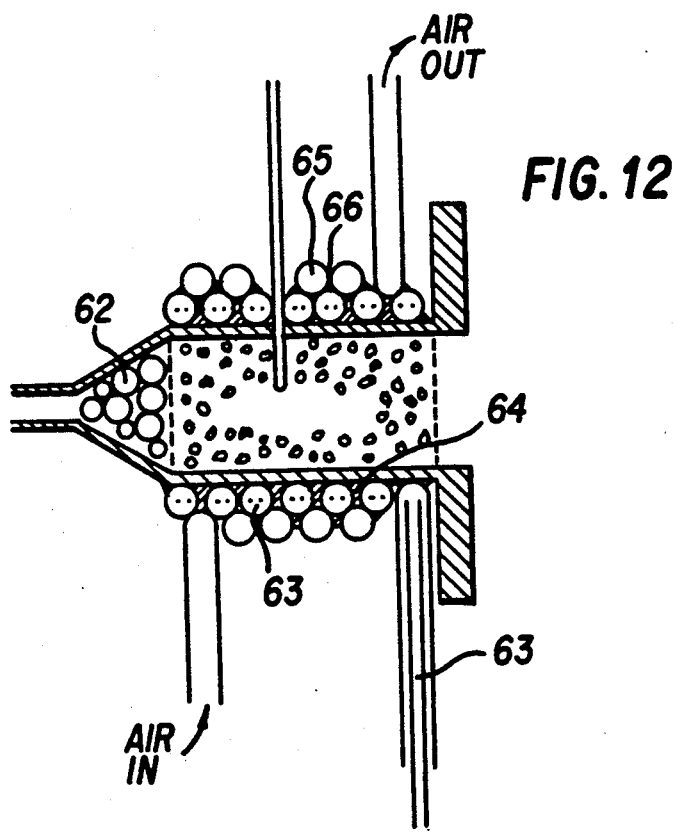

Set forth in FIG. 12 is a further alternative embodiment of the reaction system of the invention. In this system, pyrex beads 62 serve as the baffling means in the inlet of the reaction chamber. Heat is supplied to the reactor by an electrical heating element 63 on the outside of the chamber. In this instance, the heating element is a ceramic cartridge type heater wound in a coil around the outside of the reactor. Silver solder 64 deposited between the heater and the outside wall of the reaction chamber comprises heat transfer means for conducting heat from the cartridge heater to the interior of the chamber. To estabish a cooling load against which the power supply to the electrical heater may be adjusted in providing temperature control, a flow conduit for a temperature regulating fluid, comprising a coil 65, is wound around the heater coil. Additional silver solder 66, deposited between the heater coil and the temperature regulating fluid coil 65, comprises means for transfer of heat from the heater coil and reaction chamber to the temperature regulating fluid.

Figure 13:
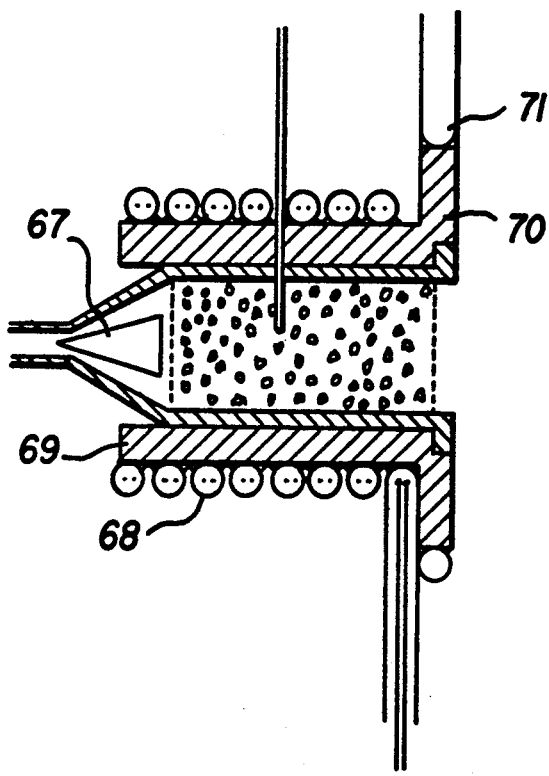
FIGS. 11–13 illustrate alternative reaction systems for use in the TAPRS.

A further emodiment of the reaction system of the invention is illustrated in FIG. 13. As baffling means, this system may utilize any of the means described above, but the drawing shows the use of a conical baffle 67 of a configuration somewhat different from that of the conical baffle 50 of FIG. 8. Heat is supplied by an electrical heater 68 comprising a coiled cartridge type heater surrounding the chamber. A sleeve 69 of copper or other high conductivity material, telescoped over the reaction chamber inside of the heating coil, distributes heat flowing either into or out of the reactor. Sleeve 69 terminates in a flange 70 at the exit end of the reaction chamber. A temperature regulating fluid conduit 71 is welded to the periphery of the flange. Fluid, typically air, flowing through conduit 71 establishes a cooling load on the system and assists in the fine regulation of temperature inside the reactor.

In addition to their utility in TAPRS systems, the reactors illustrated in FIGS. 8 and 11-13 may be used as microreactors to obtain scaleup data on the net (overall) reaction for a catalytic synthesis. By charging the reactant gases continuously and reacting under conditions considered of interest for commercial operations, a product gas may be generated, and this gas may be subjected to conventional analyses for determination of product composition and yields. In such applications, real time analysis is normally unnecessary because transient intermediates have generally been consumed by the time the process flow stream leaves the catalyst zone. Thus, for example, chromatographic analysis of the product gas may be appropriate in such instance.

It should be understood that the manifold illustrated in FIG. 8 has application beyond the TAP system, and may be used for the introduction of gases into other gas processing systems. The manifold is particularly suitable for the mixing of low pressure gases and introduction of the resulting mixture into a gas processing system with minimal residence time of the mixture upstream of the gas processing system. The systems of FIGS. 8 and 9 have further general application for the heating of low pressure gases. More particularly, the means provided for heating the inlet gas in the inlet conduit 38 may be used for applications other than the heating of a gas for introduction into a TAP instrument.

EXAMPLES

In the Examples, the following procedure was used, with a TAPRS similar to the schematic in FIG. 1.

A sample of the catalyst was prepared and sized to 500 ±50 microns, and charged to the reactor with a catalyst zone about 0.635 cm in diameter and about 1.27 cm in length. The reactor was placed in the enclosure, which was evacuated.

A blend of reactants was prepared and was fed to a high speed pulse valve. The valve was set to introduce a pulse with an average duration, measured at full width, half maximum of about 200 microseconds. The pressure of the feed gas was adjusted so that approximately $10^{15}$ molecules entered the reactor with each pulse.

The intensity variation of the indicated mass within a particular pulse was scanned as a function of time.

Three time points could be calculated as appropriate for the type of experiment being conducted.

One is simply the time of maximum intensity, also called the time of peak maximum (TPM).

The second is the median residence time (MRT), which is the time at which 50% of the molecules of interest within a particular pulse have exited the reactor. Since the area under the curve, for a plot of mass intensity versus time is directly related the number of molecules that have exited the reactor, the MRT is the time at which 50% of the curve area is realized, or the time at which the area under the curve to that point is equal to $\frac{1}{2}\int I(t)dt$, where I(t) is the observed mass intensity as a function of time.

The third is the average residence time or the time-weighted residence time, tr, which is most conveniently obtained directly from the mass intensity curve by evaluating the following expression:

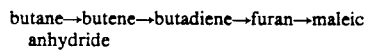

where t is time and I(t) is the observed mass intensity as a function of time.

EXAMPLE 1

A catalyst of the composition $V_1P_{1.05}O_x$ was prepared according to the procedure of Examples 1 of U.S. Pat. No. 3,907,707, which is incorporated herein by reference. A 0.5 g sample of the catalyst was charged to the reactor. The reactor was placed in the TAPRS and the enclosure was evacuated. The temperature of the reactor was maintained at about 500° C.

The reactant gas was a blend of about 30 mole % butane and about 70 mole % oxygen with an absolute pressure of about 120 torr. The mixture was pulsed into the reactor.

The analysis of the resolved product pulse indicated masses at 54, 56, and 68, which correspond to butadiene, butene, and furan. The TMP's were as follows: butane, 8.5 milliseconds; butene, 10.5 milliseconds; butadiene, 14.5 milliseconds; and furan, 22 milliseconds.

Since this catalyst converts this feed gas into maleic anhydride, the data above indicate that butene, butadiene, and furan are all intermediates in that reaction. The various TPM's indicate that the reaction sequence is as follows:

butane→butene→butadiene→furan→maleic anhydride

Figure 2:
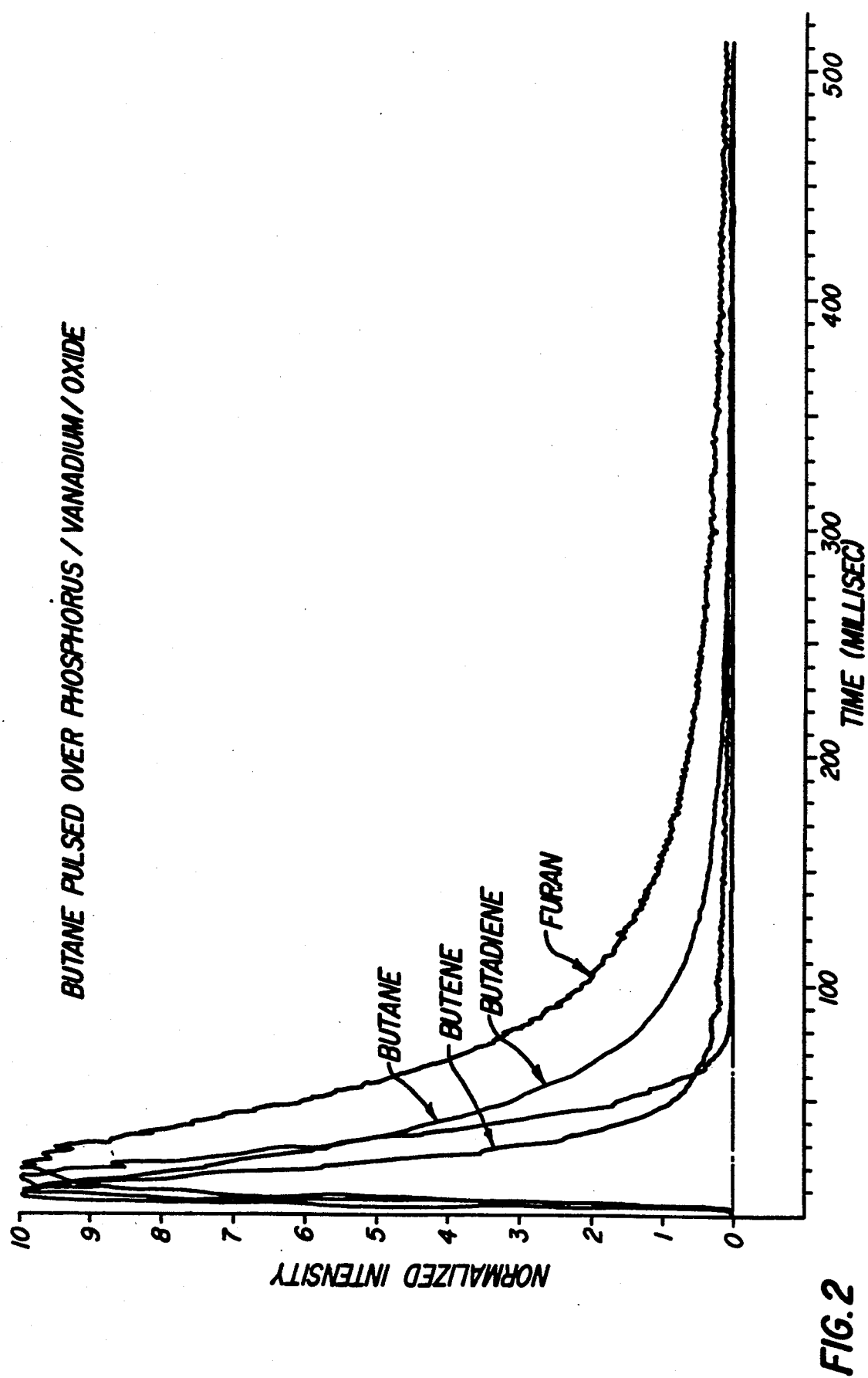
FIGS. 2-5 are examples of data obtained from TAP experiments and will be discussed with the Examples.

The plots of the normalized intensity curves for butane, butene, butadiene, and furan are shown in FIG. 2.

EXAMPLE 2

A catalyst of the following composition, $MN_{1.25}PO_x$—50 wt. % $SiO_2$ was prepared according to the procedure of Example 1 of U.S. Pat. No. 4,457,905, which is incorporated herein by reference. In a conventional fluid bed reactor, at 450° C., a mixture of 7.2% $NH_3$, 7.0% $CH_3OH$, 18% $O_2$, and the balance inert, produced HCN in 88% yield.

A 0.45 g sample of the catalyst was placed in the reactor, which was placed in the TAPRS as above. The reactor was maintained at 450° C.

A reactant gas blend was prepared of about 28.6 mole % each of methanol, ammonia, and oxygen and about 14.3% argon with an absolute pressure of about 245 torr. This mixture was pulsed into the reactor.

Figure 3:
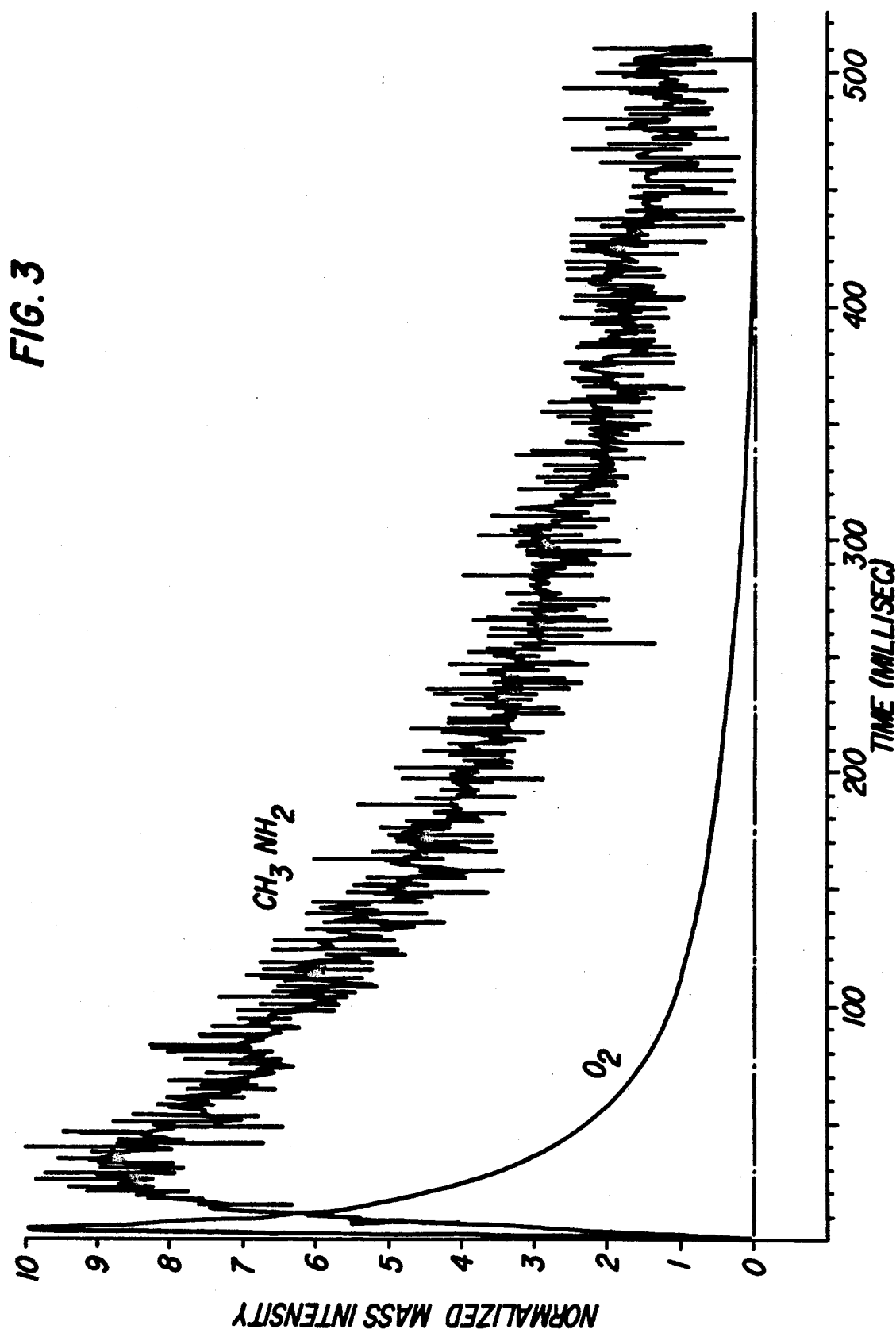

Analysis of the product gas indicated formation of methylamine, mass 30, but no measurable HCN, mass 26, was formed. FIG. 3, which shows the curves for oxygen and methylamine, helps to explain the lack of HCN formation. When the intensity curve for methylamine is at its peak, about 40 milli-seconds, the intensity curve for oxygen is far past its peak, so that oxygen is not present in the reactor in sufficient quantities for further reaction of the methylamine. This could be solved by either pulsing oxygen somewhat later than the remainder of the gas mixture, or by feeding oxygen on a continuous basis.

Another set of runs was performed in which molecular oxygen was fed continuously during pulsing, and hydrogen cyanide and water were produced as expected.

This Example demonstrated that methylamine is an intermediate in the reaction and that oxygen is required for the methylamine to complete the reaction.

EXAMPLE 3

A sample 0.5 g of $Bi_2MoO_6$, gamma bismuth molybdate, as commercially available, was placed into the TAPRS. Gamma bismuth molybdate is known to catalyze the formation of acrolein from propylene and oxygen.

Knowledge of the desorption energy of the acrolein is important for assessing selectivity losses after product formation. TAP can be used to determine the desorption energy, $E_d$.

At constant temperature, in a TAP experiment, the time-weighted residence time tr is related to the rate of desorption, $k_d$, by the following expression:

$$tr = C[1 + (k_a/k_d)]$$

where $k_a$ is the rate of adsorption and C is a constant dependent upon configuration of the catalyst.

From this it can be shown that a plot of $\ln[tr - tr']$ where tr is the time-weighted residence time of acrolein, and tr' is the time-weighted residence time of an inert gas, such as argon, versus 1/T, where T is temperature in degrees Kelvin gives a straight line with a slope of $E_d/k$, where k is Boltzmann's constant from the Arrhenius expression. Thus $E_d$, the desorption energy, can be determined.

Figure 4:
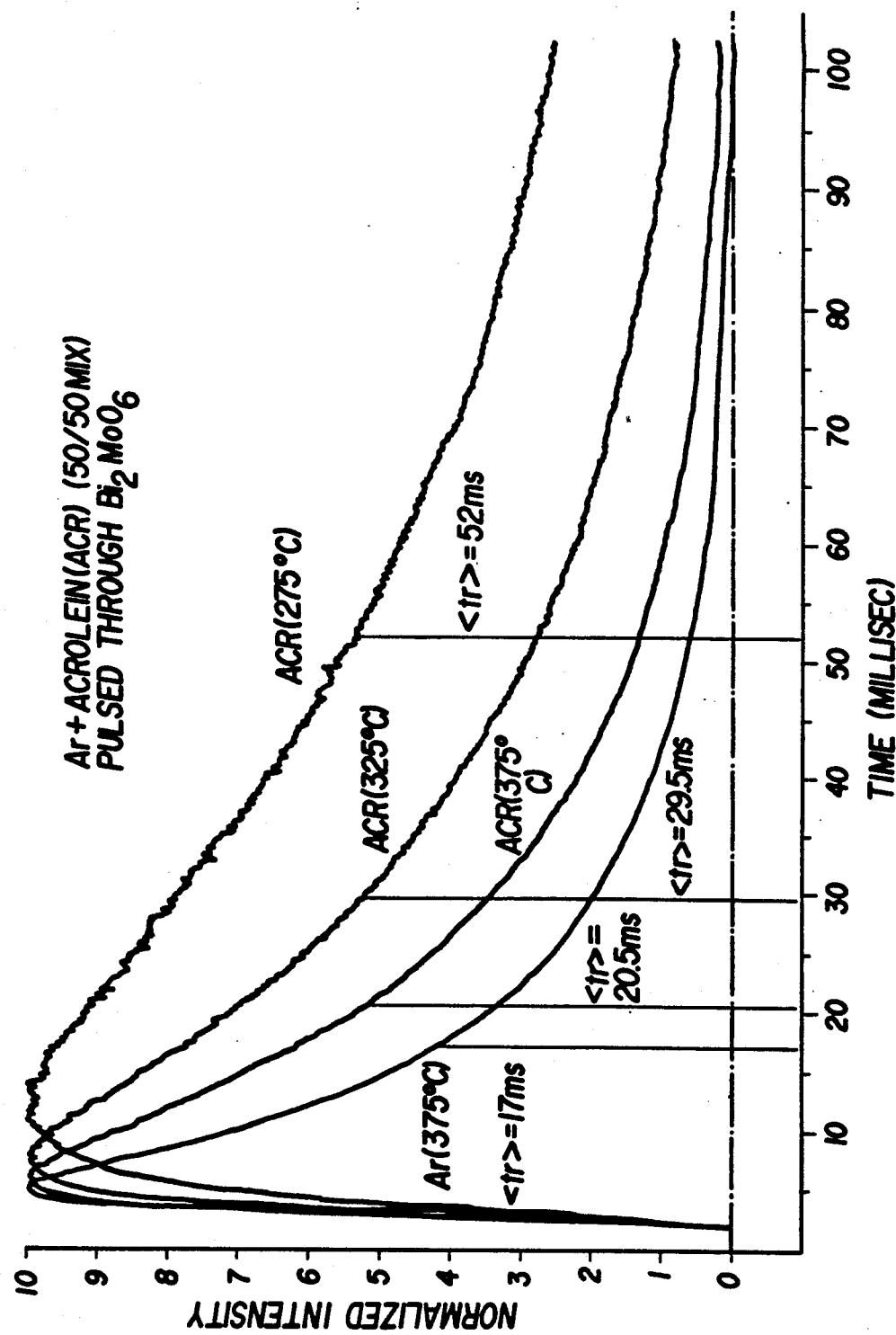

A blend containing about 50 mole % each of acrolein and argon with an absolute pressure of about 50 torr was pulsed into the reactor containing the gamma bismuth molybdate over varying temperatures. Examples of some of the curves obtained, with labeled tr times are shown in FIG. 4.

Figure 5:
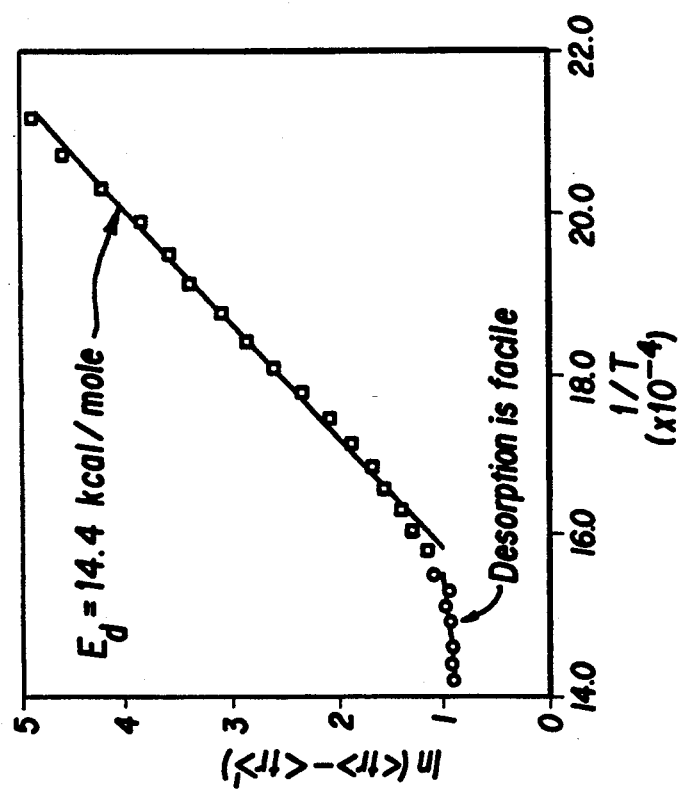

Analysis of all of the data gives a plot shown in FIG. 5. Below about 625° K., the desorption energy is about 14.4 kcal/mole. Above about 625° K. desorption becomes facile, and we can infer that the surface has changed. Importantly, the best catalytic activity is best above about 625° K.

EXAMPLE 4

Two types of TAP experiments were performed. The first type was a double pulse experiment in which one reactant was pulsed into the reactor a short interval of time before the other. The intensity variation in a single product pulse was then monitored in traditional TAP fashion. The second type was a long interval experiment in which a single reactant was pulsed into the microreactor at a high repetition rate and the intensity variation in a large number pulses for a single product was monitored over an extended interval of time. The first type of experiment was used to probe rapid changes in product intensities and second type was used to monitor slower changes due to changes in the state of the catalyst surface.

The catalyst sample used in this study is described in Example 1. A reactor charge was 0.3 grams of catalyst 0.3 mm in diameter. In a typical experiment the microreactor was loaded with a catalyst charge and heated to reaction temperature under vacuum. All experiments of this example were performed at 450° C. Once the catalyst had reached reaction temperature, $O_2$ was pulsed over the catalyst and $CO_2$ production was monitored. When $CO_2$ production had ceased the catalyst was assumed to be in a fully oxidized condition and ready to be tested.

The reactants used in this study were furan, butene, butane, and oxygen. Hydrocarbon pulse intensities were set at $6 \times 10^{16}$ molecules per pulse and the oxygen pulse intensity was set at $3.6 \times 10^{17}$ molecules per pulse. Assuming a surface area of 20 sq. meters per gram for a standard catalyst sample each hydrocarbon pulse could address about a ten-thousandth of the total surface.

Furan Reaction

Figure 14:
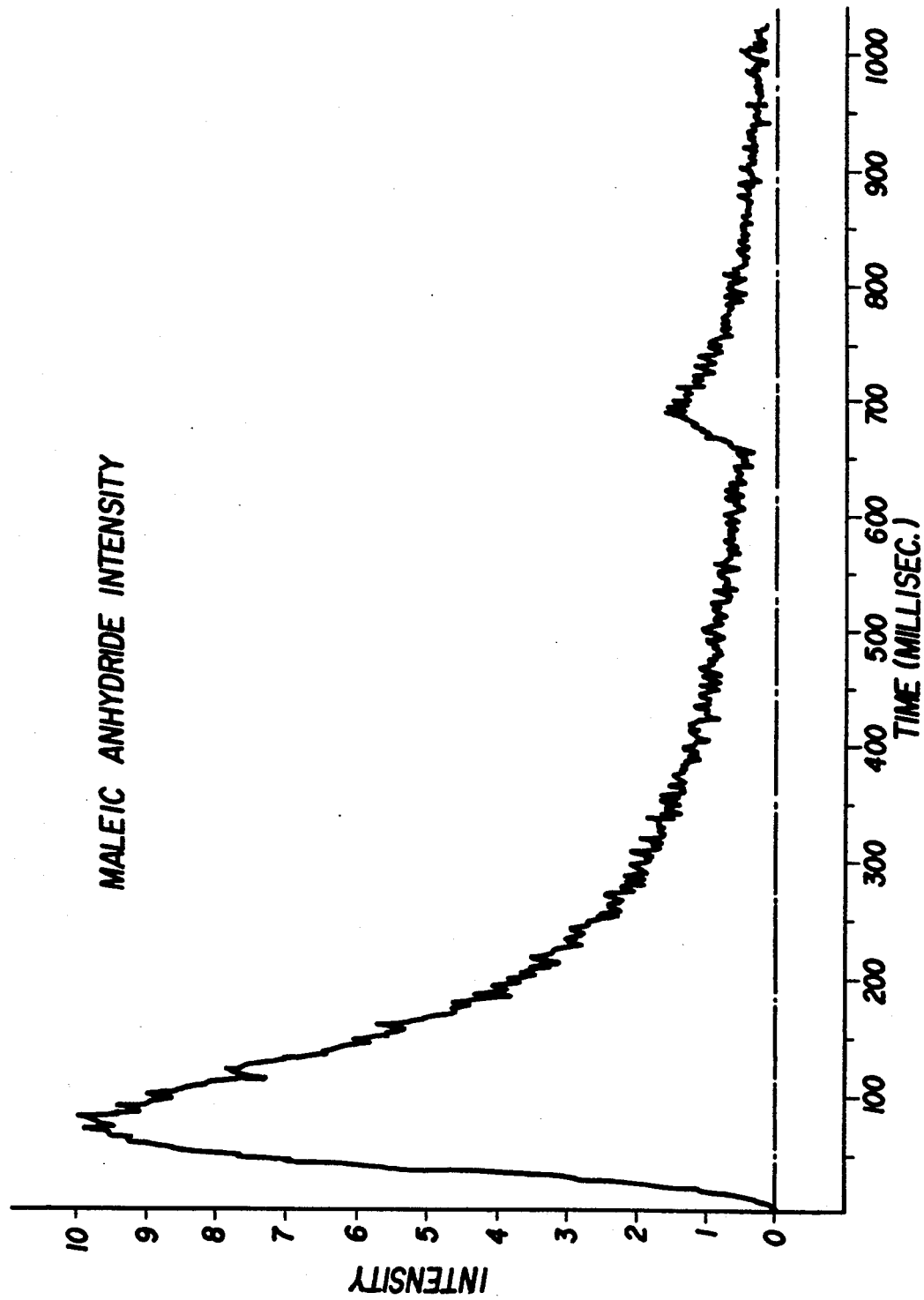
FIGS. 14–28 are further examples of data obtained by TAP experiments, as discussed in Example 4.
Figure 15:
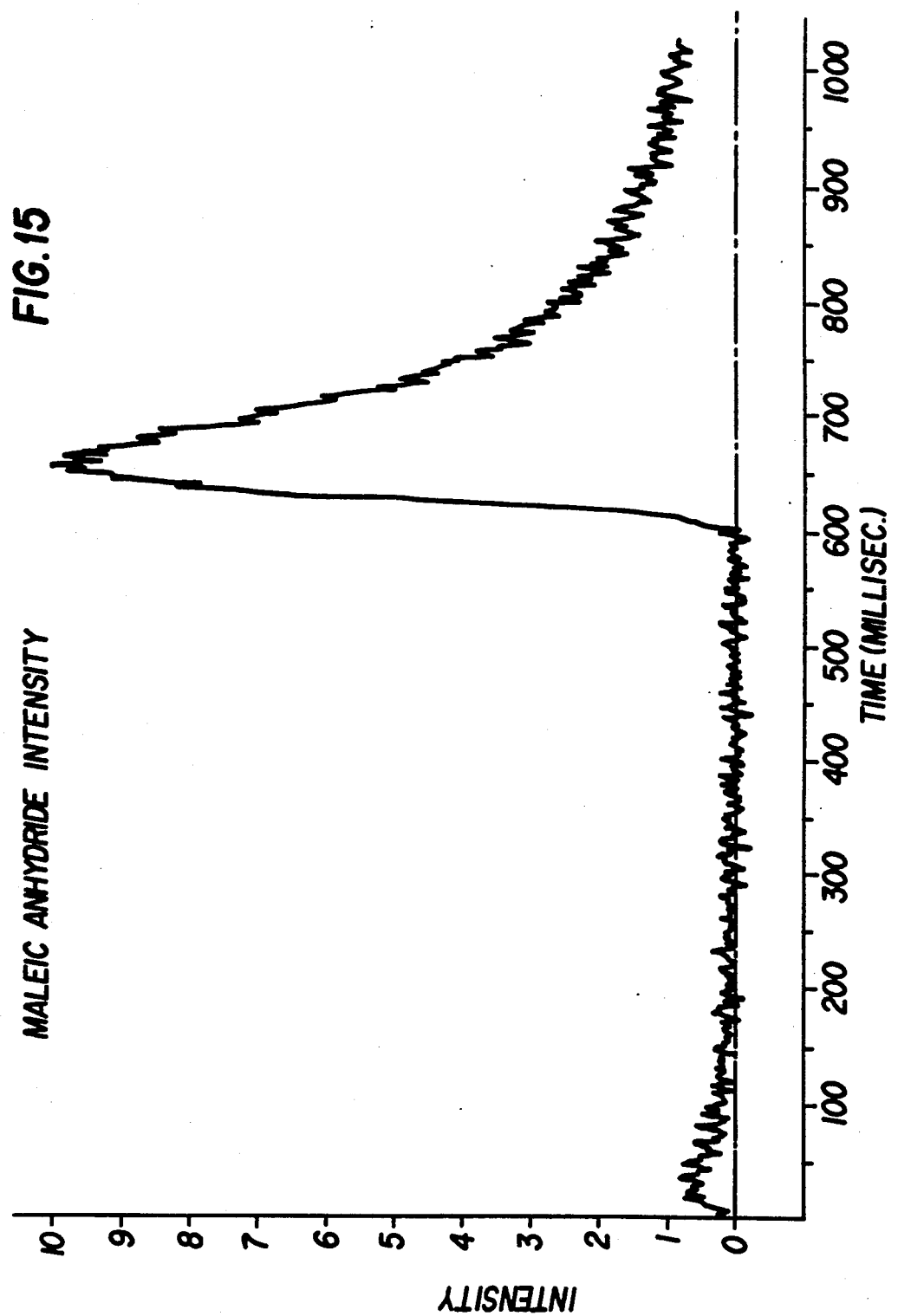
Figure 16:
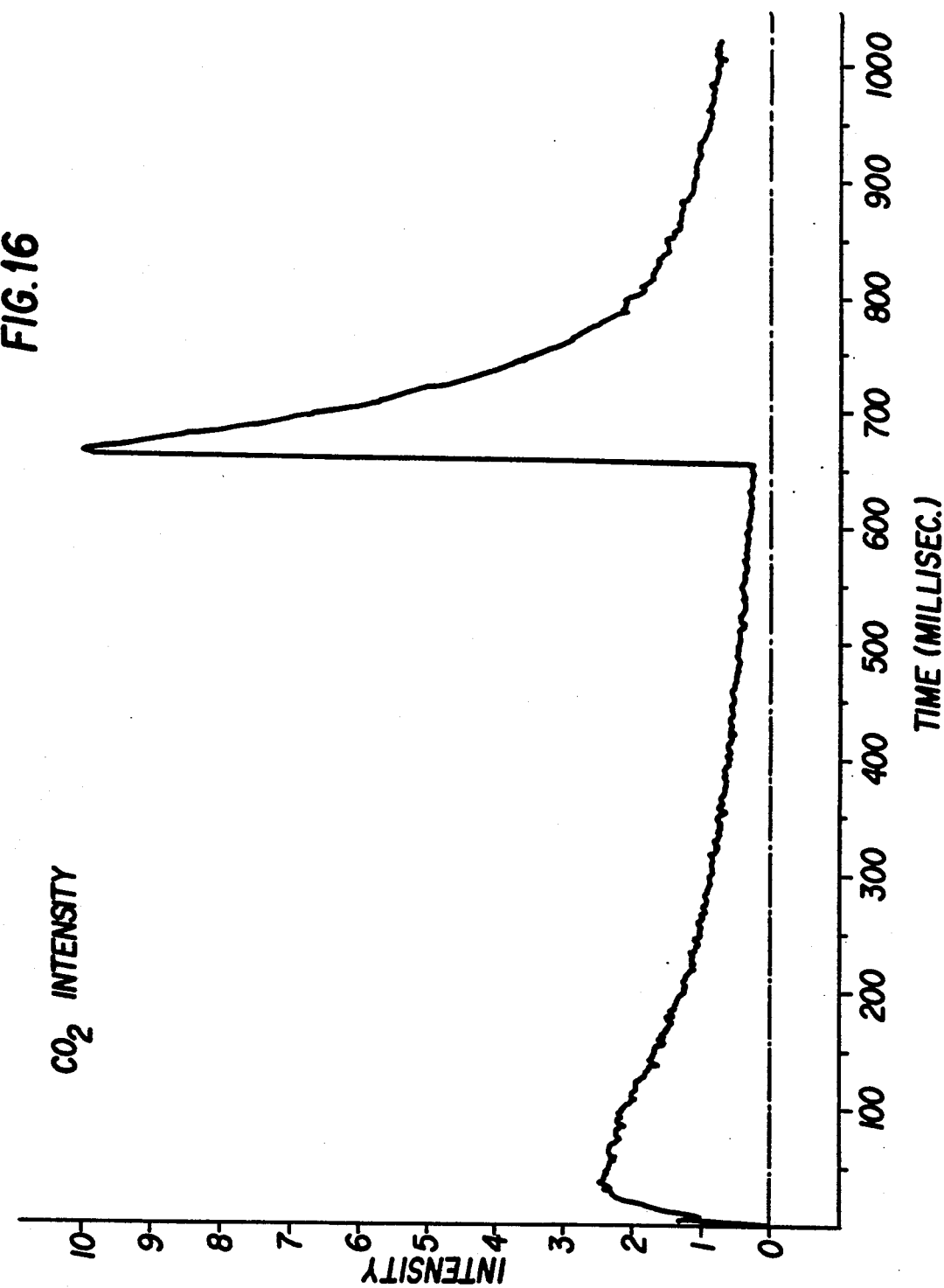
Figure 17:
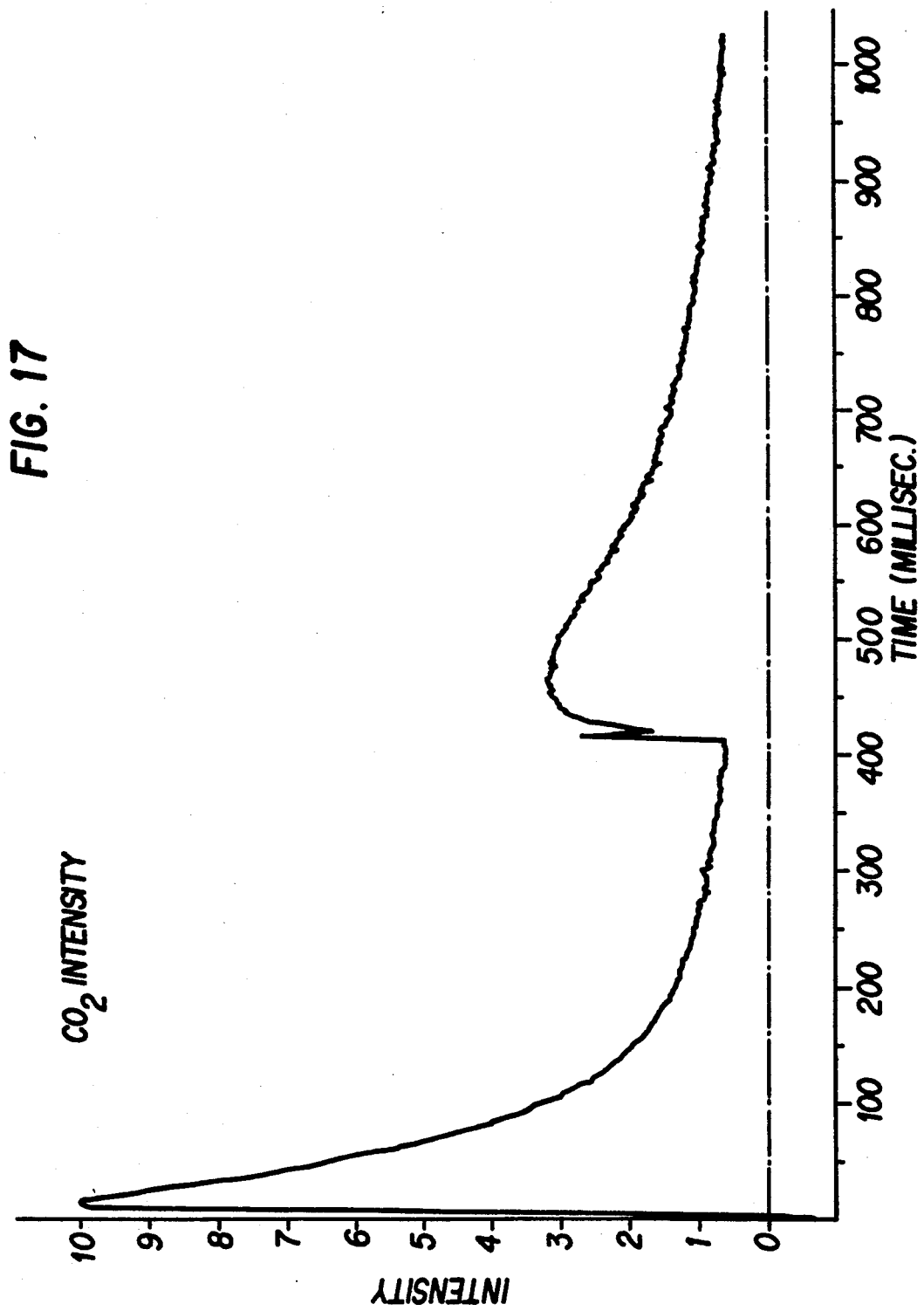

When furan is pulsed over a PVO catalyst, maleic anhydride and $CO_2$ can be observed as products. In FIGS. 14 and 15 the maleic anhydride pulse intensity variation from a typical double pulsed experiment is shown. Curve 14 results when furan is pulsed into the reactor first followed by an $O_2$ pulse 650 milliseconds later. Curve 15 results when $O_2$ is first pulsed into the reactor followed by furan pulse 600 milliseconds later. In each case the maleic intensity is greatest when the furan pulse moves through the reactor. In FIGS. 16 and 17 the $CO_2$ pulse intensity is shown in a smiliar type of experiment. Curve 16 results when furan is pulsed first and curve 17 results when $O_2$ is pulsed first. Unlike the maleic yield a sizeable $CO_2$ pulse occurs when the $O_2$ pulse moves through the reactor.

Figure 18:
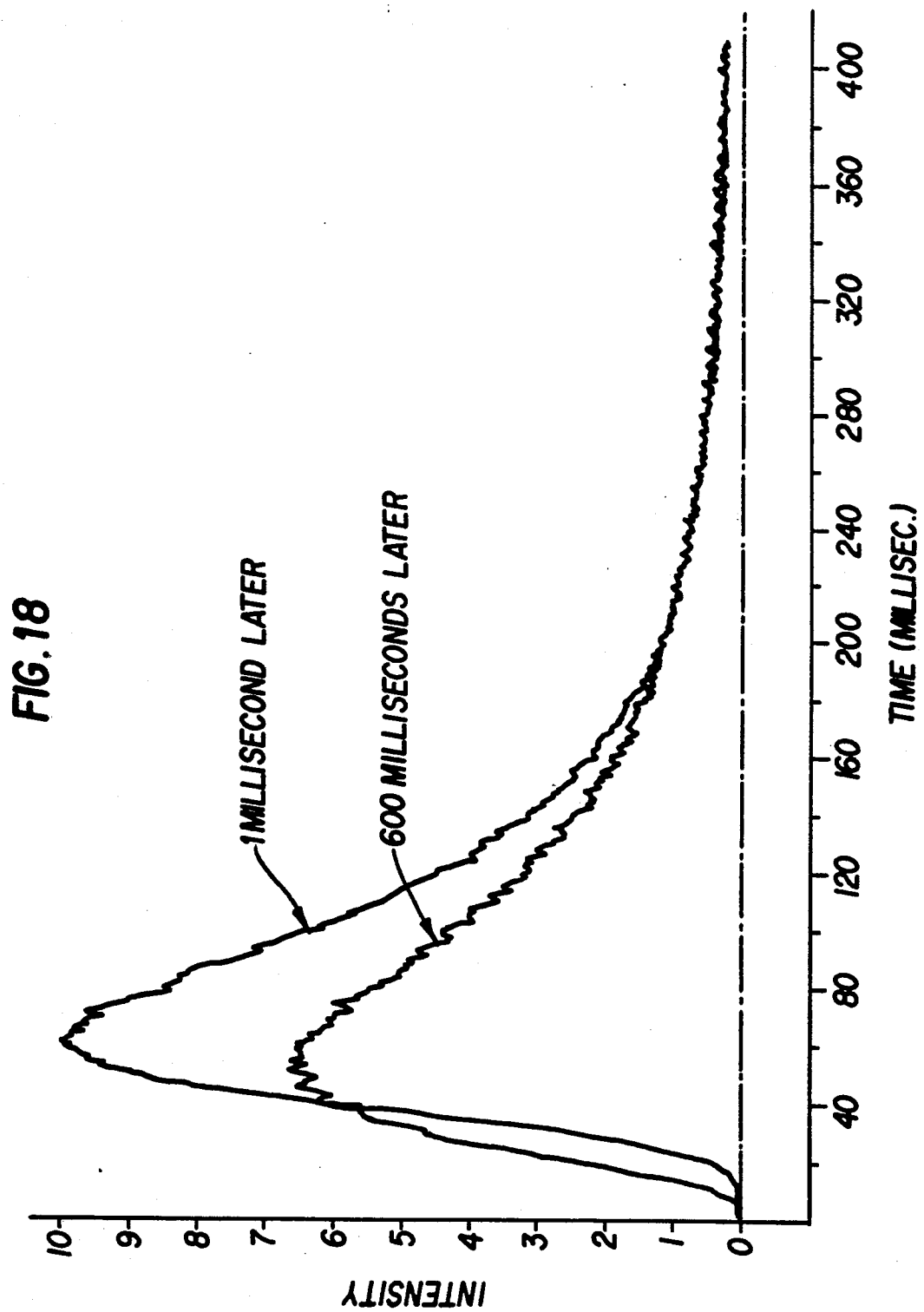

The curves shown in FIG. 18 illustrate how the intensity of the maleic pulse varies when the interval between the furan and oxygen pulse is changed. In these experiments $O_2$ was pulsed first and furan was injected at 1 and 600 milliseconds later. The signal averager was triggered at the firing of the furan pulse so the oxygen product pulse does not appear and the maleic pulses resulting from the furan appear to occur at the same time. In actuality the smaller pulse resulted when the furan was separated from the oxygen pulse by 600 milliseconds.

Figure 19:
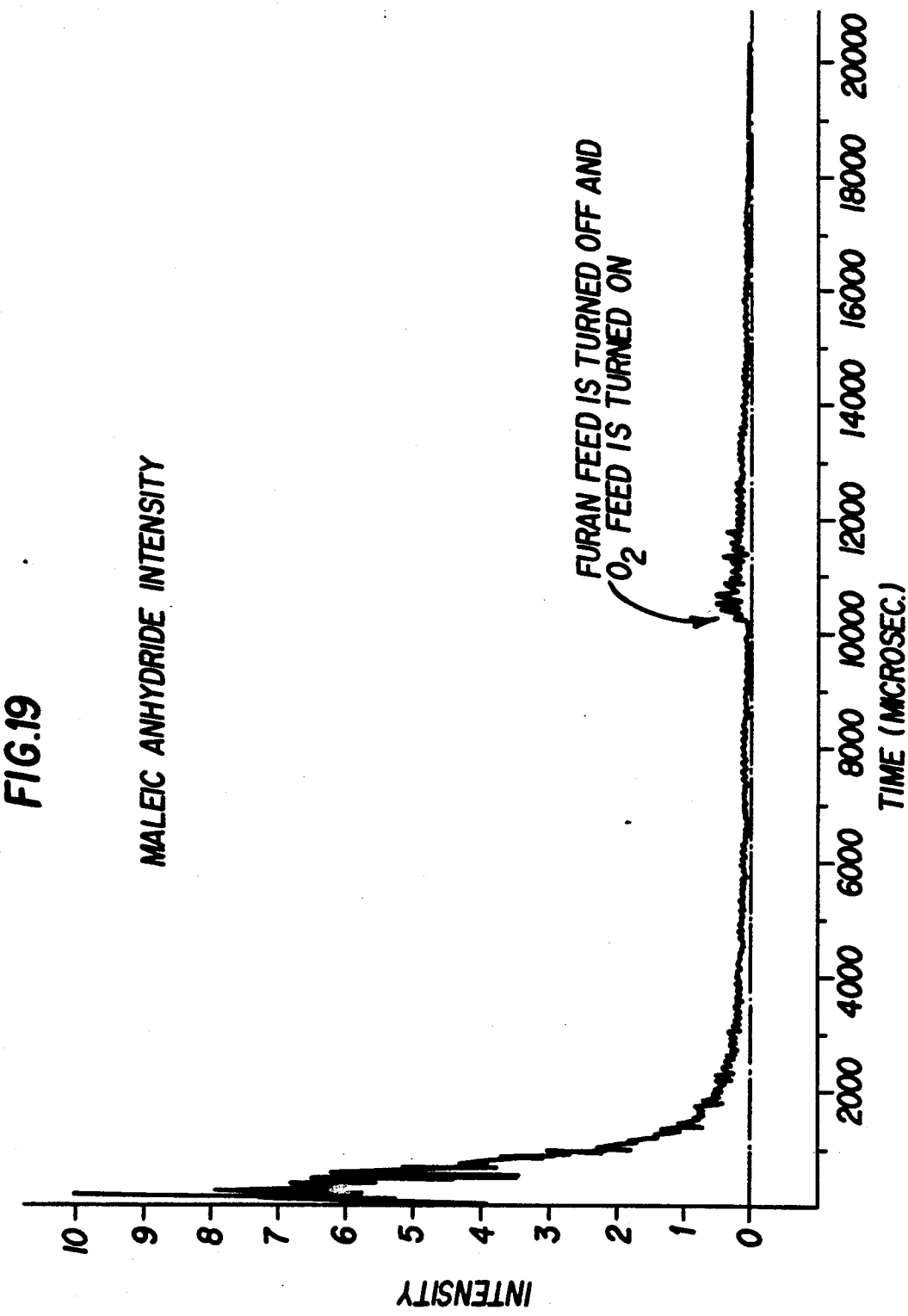
Figure 20:
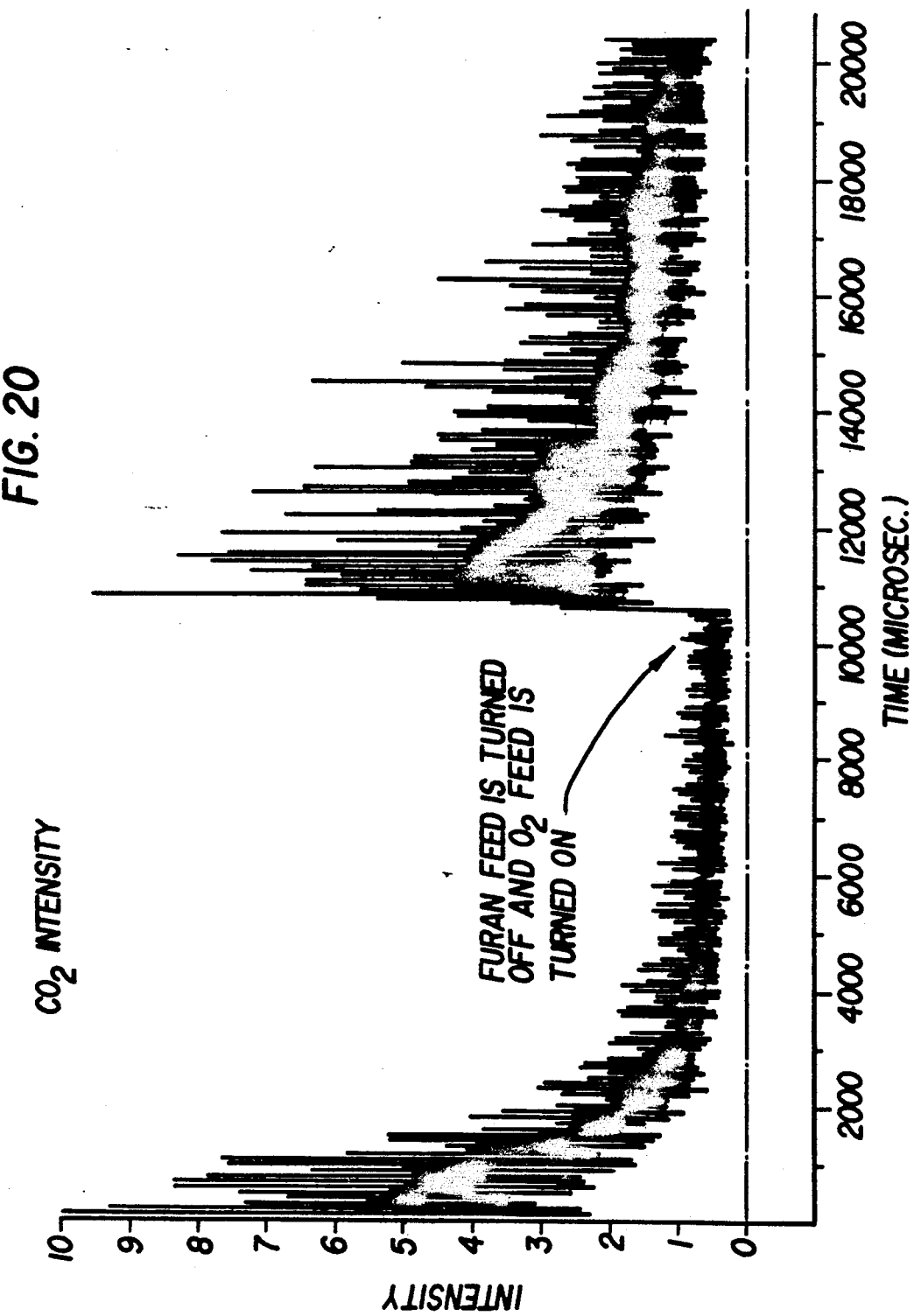

In FIGS. 19 and 20 the results of two long interval experiments are depicted. In these experiments furan was pulsed over a freshly oxidized catalyst at 40 pulses per seconds. In FIG. 19 the maleic anhydride intensity was monitored for 20 seconds and in FIG. 7 the $CO_2$ intensity was monitored for 20 seconds. In both experiments the furan feed was turned off after approximately 10 seconds and $O_2$ was pulsed into the reactor. The apparent noise in these spectra are actually individual product pulses. The regular variation in the intensity of the individual peaks which is particularaly pronounced in the $CO_2$ spectrum is due to an artifact of the signal average.

Figure 21:
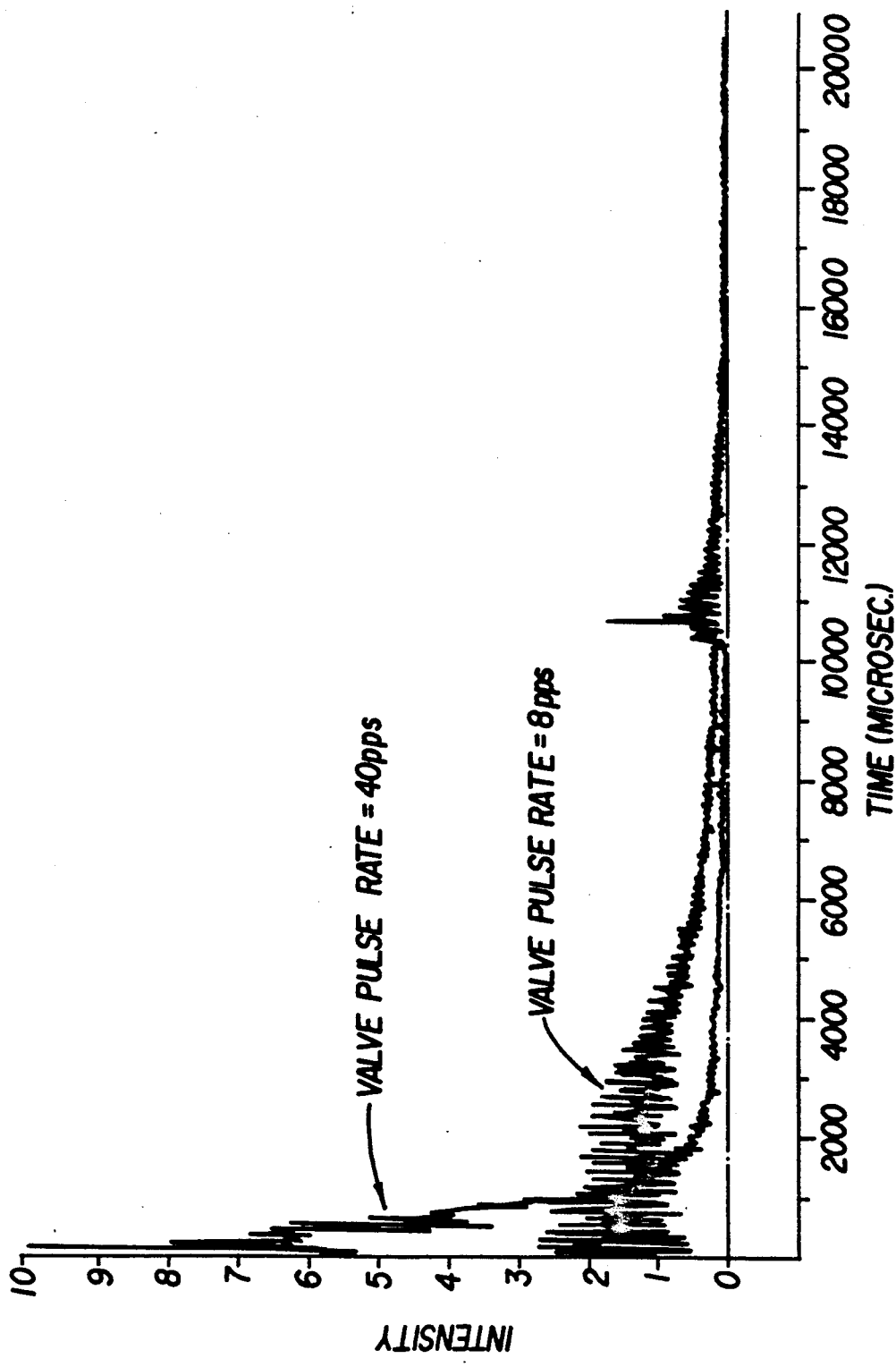

In FIG. 21 two curves are plotted which illustrate how the intensity of the maleic yield varies with the valve pulsing rate in a long interval experiment. The two spectra are plotted so as to reflect their true relative intensities. The sharper curve occurs when the feed valve is pulsed at 40 pps and the broad curve occurs at 8 pps. Within the limits of measurement the integrated intensity of the two curves is approximately equal.

The results of the double pulsed experiments indicate that furan reacts with an adsorbed oxygen species rather than $O_2$ gas reacting with adsorbed furan. If furan were first adsorbed on the surface and then subsequently selectively oxidized to maleic it would be expected that a large maleic product pulse would occur when the oxygen pulse moves through the reactor. Instead the maleic pulse resulting from the oxygen pulse is 50 times smaller then that resulting from the furan pulse. In addition, the double pulsed experiments show that a large fraction of the $CO_2$ yield results from the reaction of $O_2$ gas with adsorbed furan. This is indicated by the large $CO_2$ peak which results when oxygen is injected into the reactor.

The long interval experiments indicate that a fully oxidized surface does not have a great capacity for furan oxidation.

BUTENE REACTION

Figure 22:
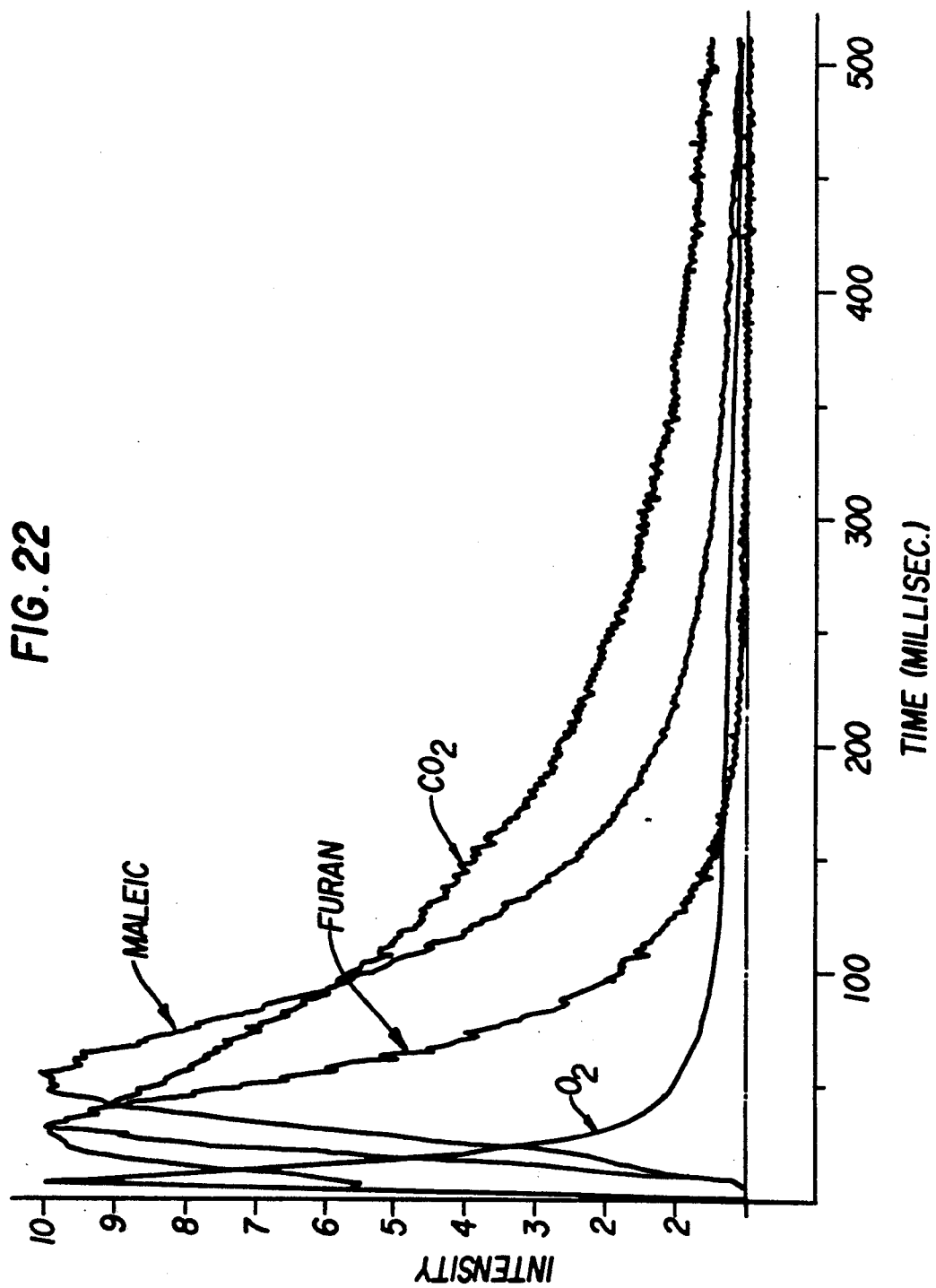

FIG. 22 shows a composite TAP spectrum resulting from pulsing $O_2$ followed 1 millisecond later by butene into the TAP reactor. The four curves shown are $O_2$, $CO_2$, furan and maleic anhydride. The intensity of the various peaks are normalized to one and do not reflect the actual yield of the products.

Figure 23:
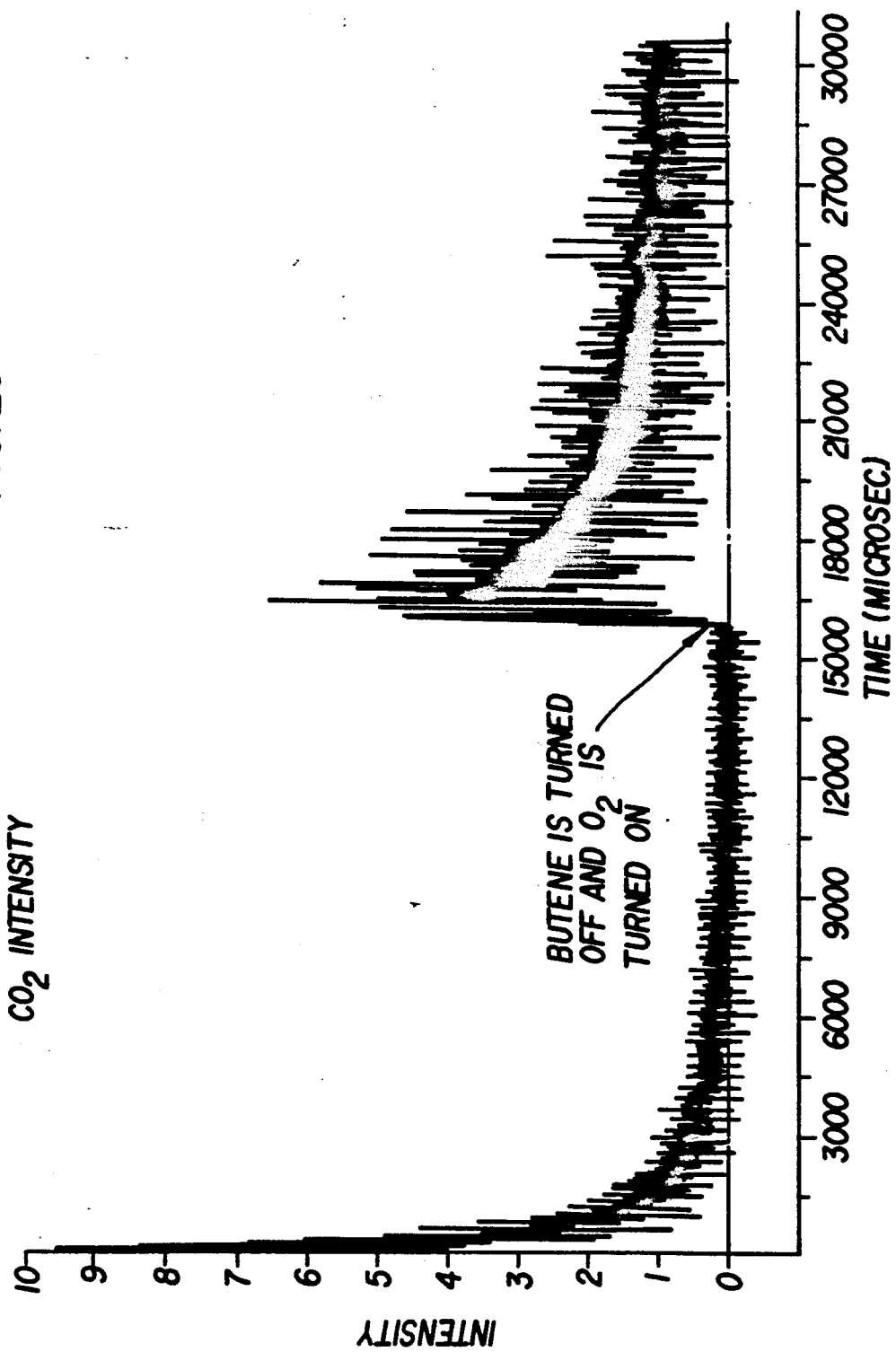
Figure 24:
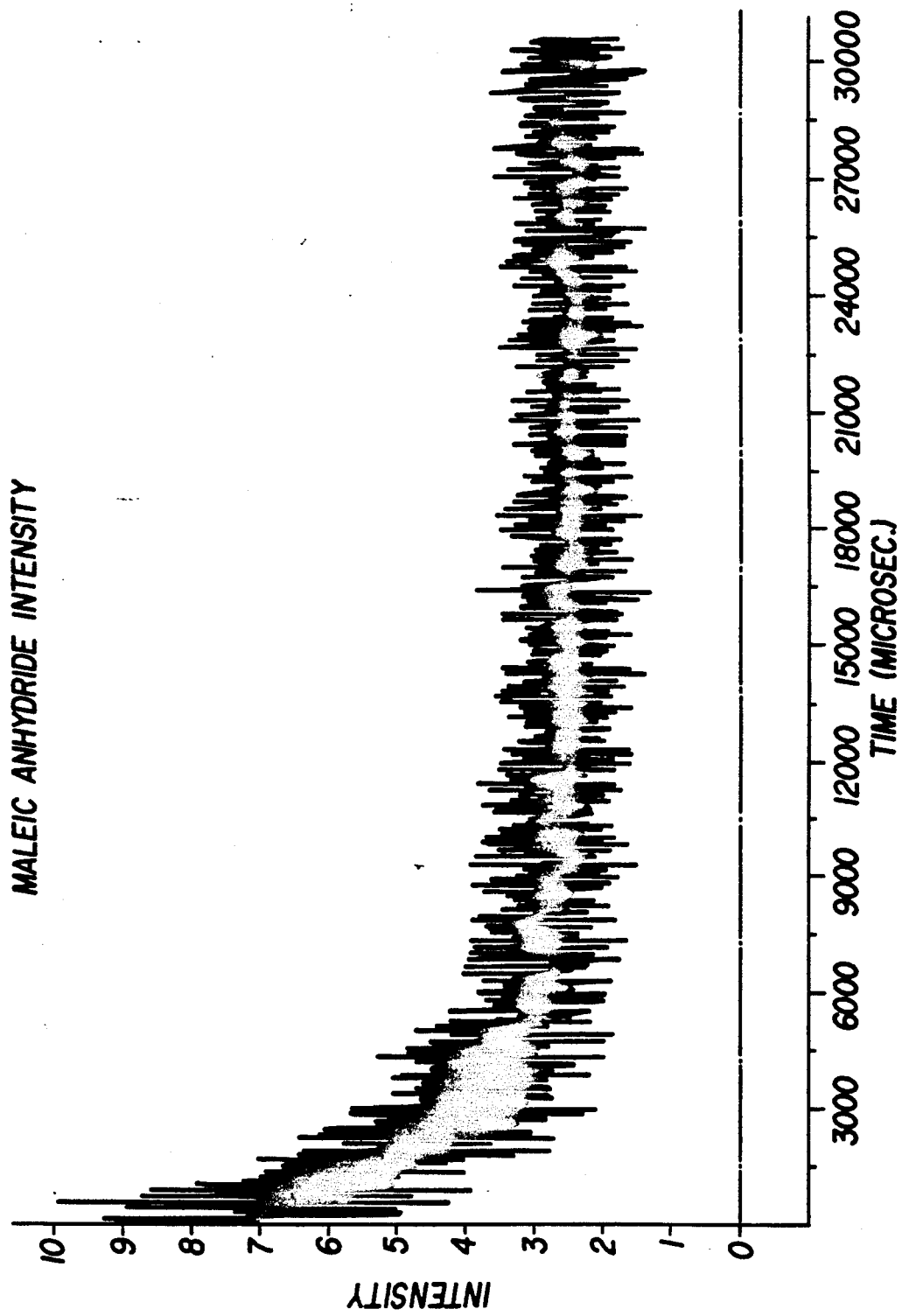
Figure 25:
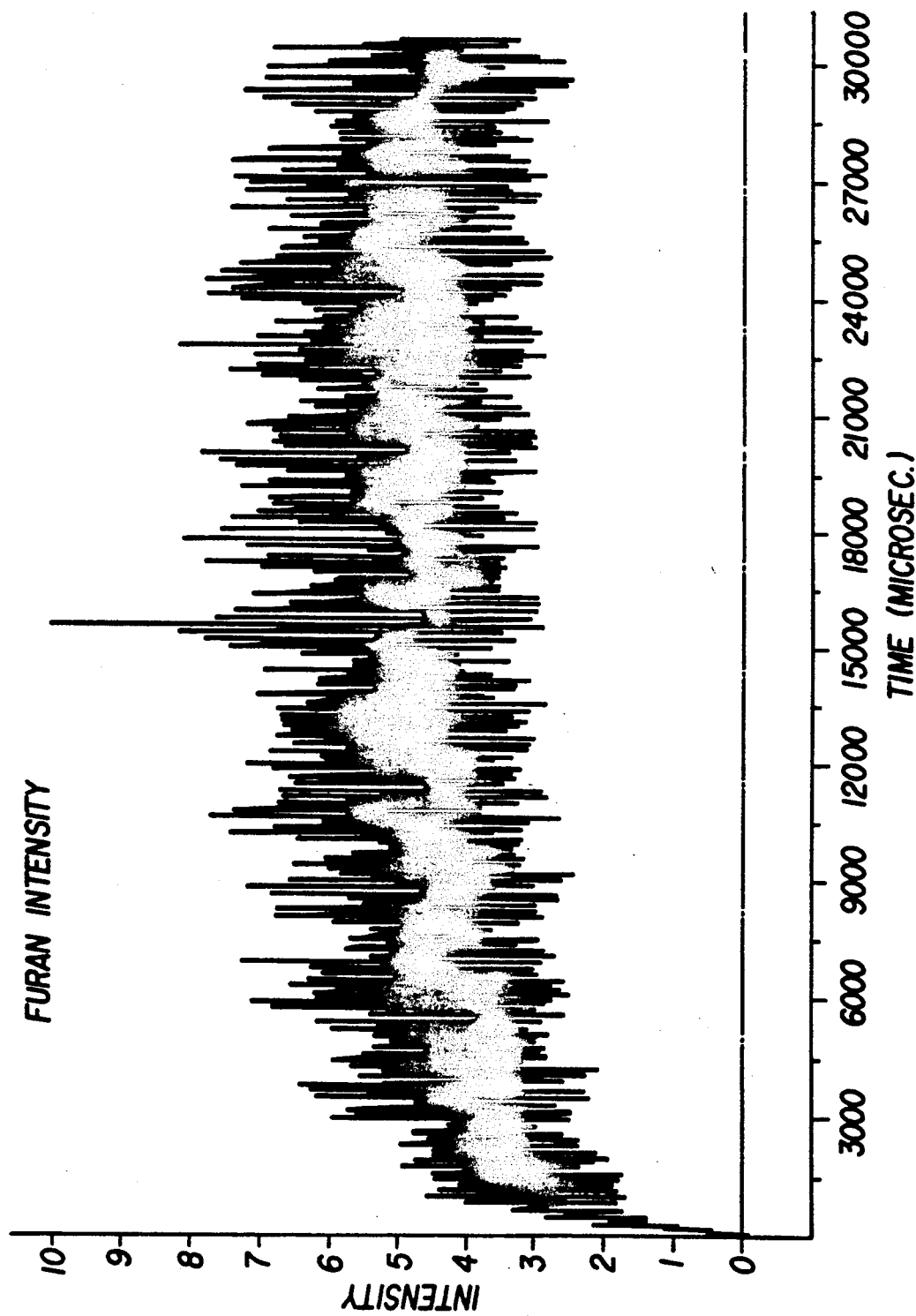
Figure 26:
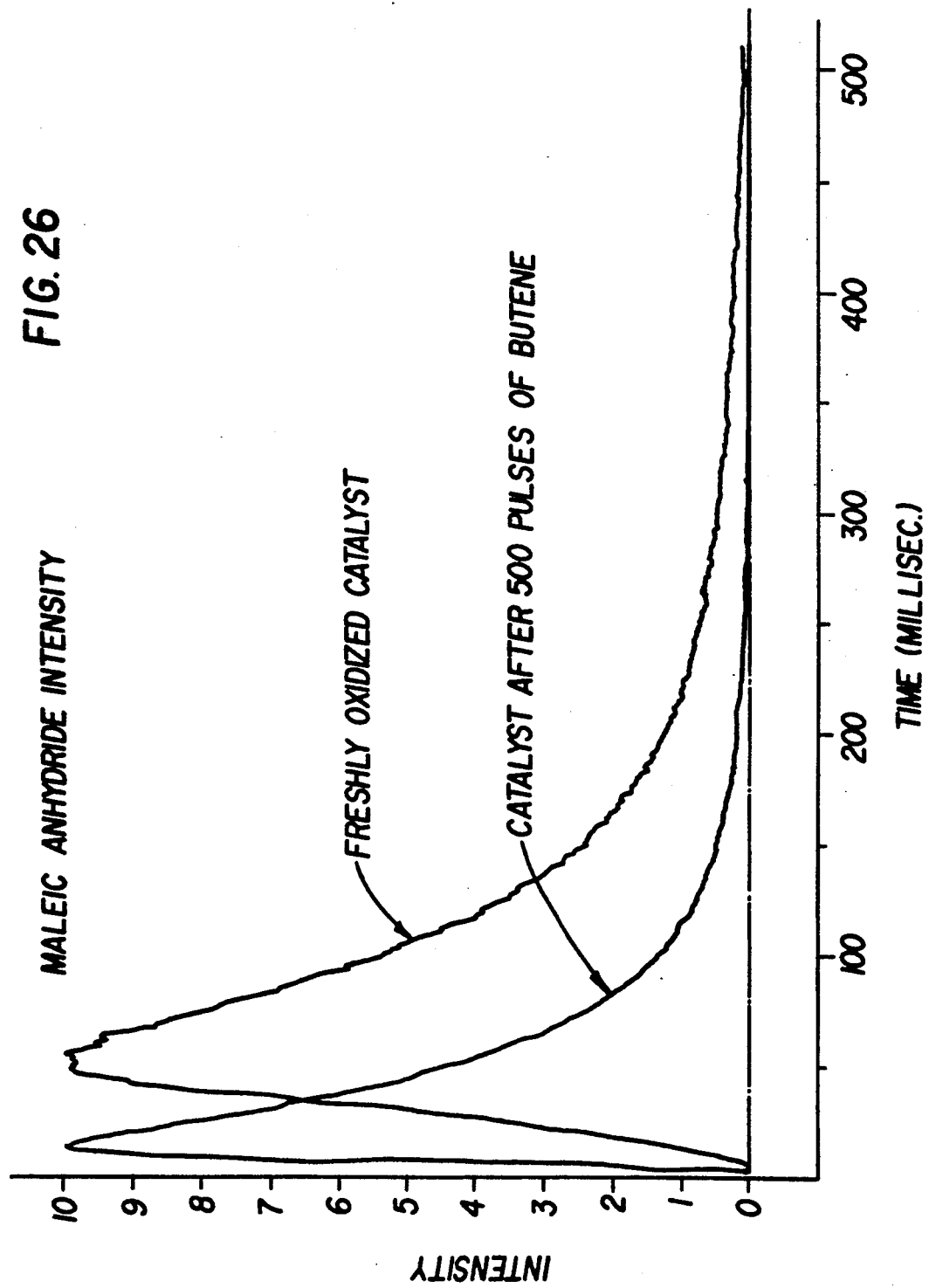

FIGS. 23, 24, and 25 are long interval experiments in which the products $CO_2$, maleic anhydride and furan are monitored over a 30 second interval. In each experiment butene was pulsed into the reactor at 40 pps. In the experiment monitoring the $CO_2$ production (FIG. 23) the butene is turned off after approximately 15 seconds and $O_2$ is pulsed into the reactor. The maleic anhydride spectra shown in FIG. 24 drops off rapidly in the first 6 seconds and appears to reach a steady state. In actuality little if any maleic anhydride is produced after the first 6 seconds. The apparent steady state production of maleic is due to the production of butadiene which has a mass peak coincident with the principal maleic peak. These peaks can be differentiated by their pulse shapes. This is illustrated in FIG. 26. The broad peak in this composite was taken during the first few butene pulses over a freshly oxidized catalyst while the narrow peak was taken after 500 butene pulses. In FIG. 25 the furan curve starts out at zero and reaches a steady state after the first few seconds. The production of furan shows no sign of decreasing in the time frame of these experiments.

The results of the butene experiments indicate that the production of $CO_2$ and maleic anhydride from butene looks remarkably similar to that produced from furan. On the other hand, the production of furan from butene clearly must proceed via a different mechanism. The result that furan production starts from zero and reaches a maximum after maleic production has stopped indicates that a different oxygen species is involved in the two reactions. Moreover, it is clear that the furan producing oxygen is far more abundant.

BUTANE REACTION

Figure 27:
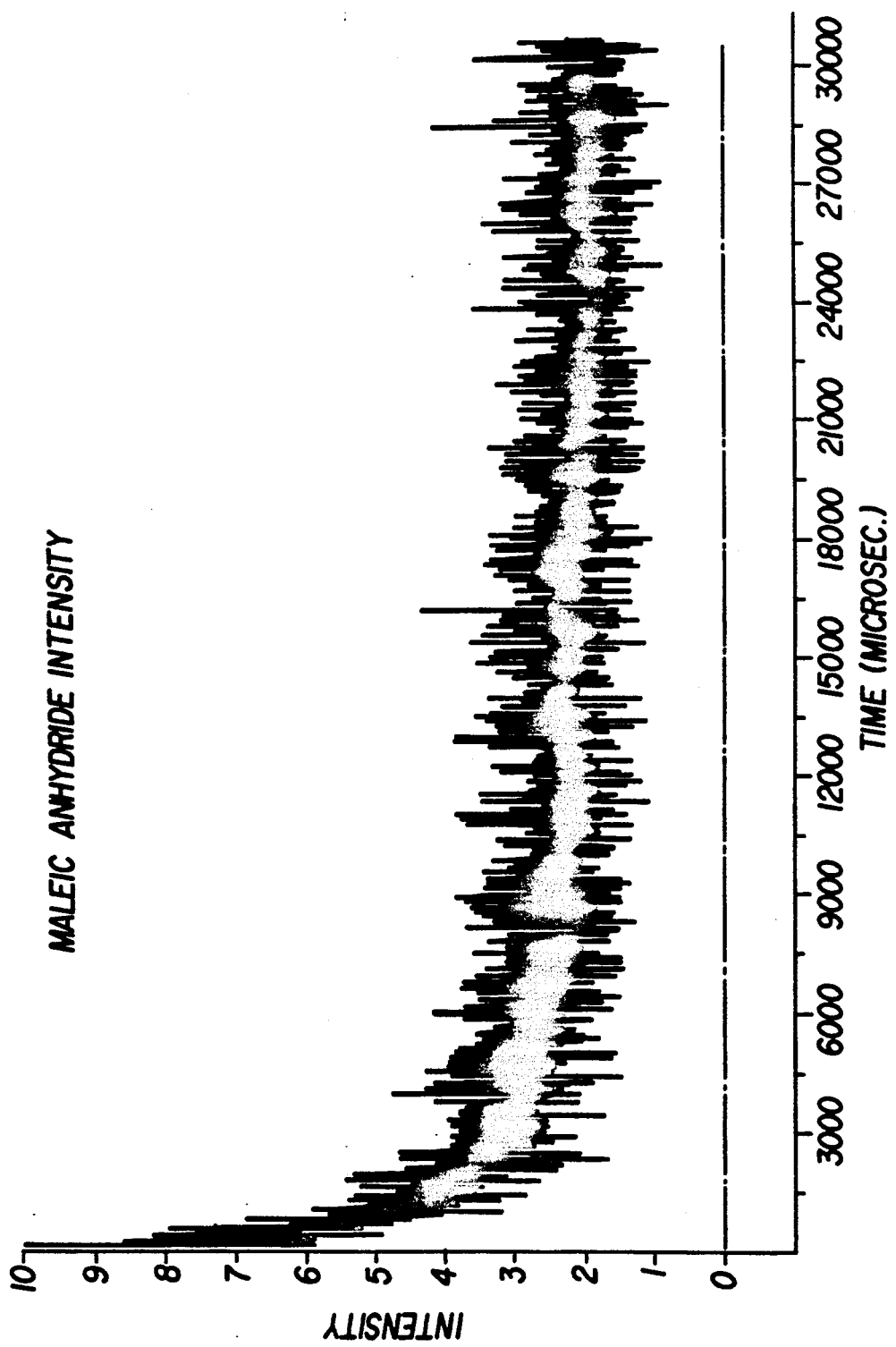

FIG. 27 shows the result of a long interval experiment pulsing butane in which the production of maleic anhydride is monitored over an interval of 30 seconds. The curve looks very similar to the equivalent butene curve. In this case, however, the steady state signal at times greater then a few seconds is most likely due to a minor fragment peak of butane rather then butadiene. Under the conditions of these experiments neither butadiene nor furan was observed as a product.

Figure 28:
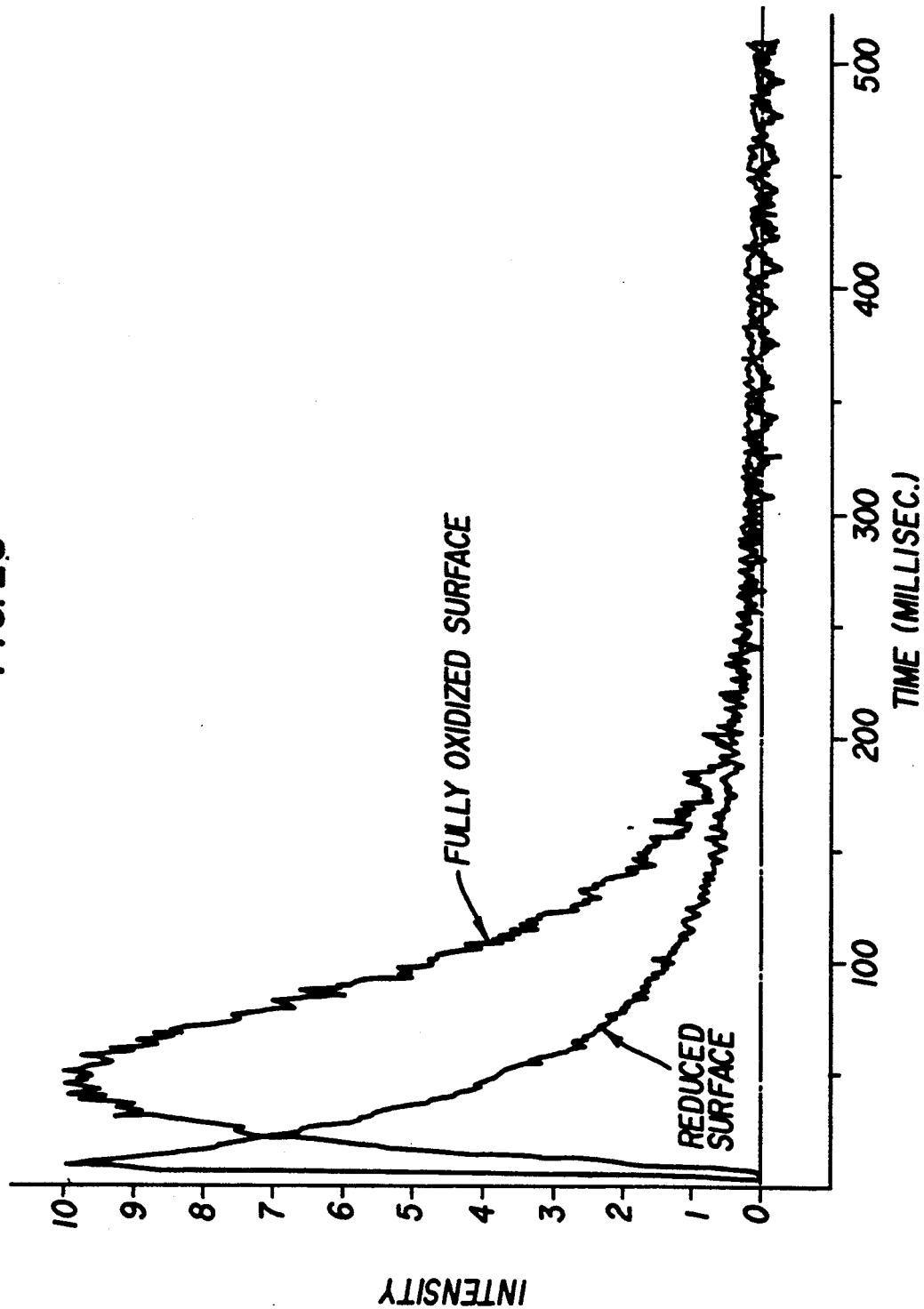

FIG. 28 is a composite spectrum of the maleic mass peak from a fully oxdized surface and the same peak after that surface has seen several hundred pulses of butane. The intensity of the two curves has been normalized to one.

The production of maleic anhydride from butane closely parallels that production of maleic from furan or butene under similar conditions. On a fully oxidized surface the maleic pulse shapes look very similar. Since the butane produced maleic does not have a significantly broader pulse shape then that coming from butene or furan it is unlikely that the former route involved desorbing intermediates. The fact that butadiene and furan are not observed in the butane reaction further confirms this. These results indicate that there are two types of oxidation sites on a PVO catalyst but that selective oxidation of butane occurs at only one. Furthermore, it would appear that $CO_2$ production when no $O_2$ gas is present is remarkably similar to maleic production, indicating that at least a portion of the $CO_2$ is produced at the selective oxidation sites.

These Examples, and the Figures, are intended as illustrative only, and are not in any way intended to limit the scope of this invention. One skilled in the art will recognize many alterations and changes that can be made from the above, without deviating from the spirit and scope of this invention.

What is claimed is:

1. An apparatus capable of use for Temporal Analysis of Products comprising a gas processing system including means which are capable of use for Temporal Analysis of Products and a manifold for introduction of a plurality of gas streams into said gas processing system, the manifold comprising a plurality of inlet channels through which gas may flow toward said system, and a mixing chamber having inlet means in communication with said plurality of channels and a chamber outlet in communication with said system, at least one of said channels having a rapidly operable gas feed valve at the terminus of the channel at which the channel communicates with said chamber inlet means, said mixing chamber having a void volume that is small relative to the working volume of the gas processing system so that the residence time of the process gases in said chamber is short compared to the residence time in said gas processing system.

2. A manifold as set forth in claim 1 comprising a metal block having a said plurality of channels contained therein, and having at least one aperture therein to accomodate the valve stem connecting said valve to a valve operator located outside said block, said aperture being closed with a bellows to which said valve stem is fixed, said valve stem extending through and being fixedly sealed to the bellows which closes the aperture that accomodates the valve stem, whereby the valve stem may be moved by the operator in opening the closing the valve without any disturbance of the seal of the manifold against ingress or egress of fluids via said aperture.

3. An apparatus capable of use for Temporal Analysis of Products comprising a gas processing system including means which are capable of use for Temporal Analysis of Products and a manifold for introduction of a plurality of gas streams into said gas processing system, the manifold comprising a plurality of inlet channels through which gas may flow toward said system, an inlet conduit for delivery of a process gas stream to said manifold, at least one of said channels being in gas flow communication with said inlet conduit, a control conduit for flow of a temperature regulating fluid, said control conduit being in heat transfer communication with said process gas inlet conduit so that heat may be transferred between said regulating fluid and a process gas flowing in said inlet conduit, said control conduit containing therewithin an electrical heater for supplying heat to the process gas stream and said regulating fluid, and a mixing chamber having chamber inlet means in communication with said plurality of channels and a chamber outlet in communication with said system, at least one of said channels having a rapidly operable gas feed valve at the teminus of the channel at which the channel communicates with said chamber inlet means, the termini of said channels at which said channels communicate with said chamber inlet means being closely adjacent each other.

4. An apparatus as set forth in claim 3 wherein said mixing chamber is integral with said manifold.

5. A manifold as set forth in claim 3 comprising a metal block having said plurality of channels contained therein.

6. A manifold as set forth in claim 5 wherein said block has a t leas tone aperture therein to accommodate the valve stem connecting said valve to a valve operator located outside said block, said aperture being closed with a bellows, said valve stem extending through and being fixedly sealed to the bellows closing the aperture which accommodates that valve stem, whereby the valve stem may be moved by the operator in opening and closing the valve without any disturbance of the seal of the manifold against ingress or egress of fluids via said aperture.

7. A manifold as set forth in claim 5 wherein said inlet conduit is contained within and aligned with said control conduit, an outside wall portion of the inlet conduit being spaced from an inside wall portion of the control conduit to define a passage between said conduits within which the regulating gas can flow.

8. A manifold as set forth in claim 7 wherein the control conduit containing the inlet conduit extends into said block through an opening in a flange mounted on said block the dimensions of said opening and the location of said control conduit being such as to provide an insulating gap between said control conduit and said flange, said block being sealed by a cap on said flange, the outer end of the cap being sealed to said control conduit.

9. A manifold as set forth in claim 5 further comprising means for heating said block by transfer of heat between said block and said regulating gas.

10. A manifold as set forth in claim 9 wherein said block heating means comprises a jacket on an outside surface of said block, the jacket on said block being in fluid flow communication with said control conduit.

11. A manifold as set forth in claim 9 wherein said block heating means comprises a cavity within said block, said cavity being in fluid flow communication with said control conduit.

12. An apparatus capable of use for Temporal Analysis of Products comprising:
an enclosed housing and means for producing a vacuum within the housing;
within said housing, a reactor having a zone defined in the reactor containing a reaction catalyst, said reactor being structured to allow a reactant gas to pass through said zone and to produce a product gas;
a manifold within said housing for introduction of a plurality of gas streams into said reactor, the manifold comprising a plurality of inlet channels through which gas may flow toward said reactor, and a mixing chamber having inlet means in communication with said plurality of channels and a chamber outlet in communication with said reactor, at least one of said channels having a rapidly operable gas feed valve at the terminus of the channel at which it communicates with said chamber inlet means, said mixing chamber having void volume that is small relative to the working volume of said reactor so that the residence time of the process gases in said chamber is short compared to the residence time in the reactor;
means for withdrawing form said reactor a pulse of product gas, within said housing, means for resolving said pulse of product gas to produce a resolved pulse of product gas in which molecules of product gas move in substantially parallel paths;
means for providing real time analysis of said resolved pulse of product gas; and
means for coordinating the actions of said rapid pulse introducing means and said analysis means so that scanning by said analysis means coincides with the arrival of a resolved pulse and of product gas and said apparatus is thereby capable of use for Temporal Analysis of Products.

13. An apparatus capable of use for Temporal Analysis of Products comprising:
an enclosed housing and means for producing a vacuum within the housing;
within said housing, a reactor having a zone defined in the reactor containing a reaction catalyst, said reactor being structured to allow a reactant gas to pass through said zone and to produce a product gas;
a manifold for introduction of a plurality of gas streams into said reactor, the manifold comprising a plurality of inlet channels through which gas may flow toward said reactor;
an inlet conduit for delivery of a process gas stream to said manifold, at least one of the channels of said manifold being in gas flow communication with said inlet conduit;
a control conduit for flow of a temperature regulating fluid, said control conduit being in heat transfer communication with said process gas inlet conduit so that heat may be transferred between said regulating fluid and a process gas flowing in said inlet conduit, said control conduit containing therewithin an electrical heater for supplying heat to the process gas stream and said regulating fluid;
a mixing chamber having chamber inlet means in communication with said plurality of channels of said manifold and a chamber outlet in communication with said reactor, at least one of said channels having a rapidly operable gas feed valve at the teminus of the channel at which it communicates with said chamber inlet means, the termini of said channels at which said channels communicate with said chamber inlet means being closely adjacent each other;
means for withdrawing from said reactor a pulse of product gas;
within said housing, means for resolving said pulse of product gas to produce a resolved pulse of product gas in which molecules of product gas move in substantially parallel paths;
means for providing real time analysis of said resolved pulse of product gas; and
means for coordinating the actions of said rapid pulse introducing means nd said analysis means so that scanning by said analysis means coincides with the arrival of a resolved pulse of product gas and said apparatus is thereby capable of use for Temporal Analysis of Products.

14. An apparatus capable of use for Temporal Analysis of Products comprising:

an enclosed housing and means for producing a vacuum within the housing;

within said housing, a reactor having a zone defined in the reactor containing a reaction catalyst, said reactor being structured to allow a reactant gas to pass through said zone and to produce a product gas;

means for withdrawing from said reactor a pulse of product gas;

within said housing, means for resolving said pulse of product gas to produce a resolved pulse of product gas in which molecules of product gas move in substantially parallel paths;

means for providing real time analysis of said resolved pulse of product gas;

a cryogenic surface surrounding the path taken by said product gas pulse as said pulse passes from said reactor to said analysis means, said cryogenic surface being cooled by a cryogenic fluid; and means for coordinating the actions of said rapid pulse introducing means and said analysis means so that scanning by said analysis means coincides with the arrival of a resolved pulse of product gas and said apparatus is thereby capable of use for Temporal Analysis of Products.

15. An apparatus as set forth in claim 14 wherein a cryogenic plate is disposed between said reactor and said resolving means, said plate having an aperture therein for passage of said pulse therethrough.

16. An apparatus as set forth in claim 15 wherein said plate comprises a metal disk having a cryogenic conduit disposed on a face thereof, said cryogenic conduit being adapted for the passage of a cryogenic fluid therethrough.

17. An apparatus as set forth in claim 16 further comprising a coating comprising a molecular sieve on the face of said plate that faces toward said reactor and away from said analysis mean.

18. An apparatus capable of use for Temporal Analysis of Products comprising:

an enclosed housing and means for producing a vacuum within the housing;

within said housing, a reactor having a zone defined in the reactor containing a reaction catalyst, said reactor being structured to allow a reactant gas to pass through said zone and to product a product gas;

means for introducing a rapid pulse of reactant gas to said reactor;

conduit means for gas flow between said pulse means and said reactor, said gas flow means comprising a reactant gas mixing zone having a void volume that is small relative to the working volume of said reaction zone, so that the residence time of gas in said reaction zone is substantially longer than the residence time of gas in said mixing zone;

means for withdrawing from said reactor a pulse of product gas;

within said housing, means for resolving said pulse of product gas to produce a resolved pulse of product gas in which molecules of product gas move in substantially parallel paths;

means for providing real time analysis of said resolved pulse of product gas; and means for coordinating the actions of said rapid pulse introducing means and said analysis means so that scanning by said analysis means coincides with the arrival of a resolved pulse of product gas and said apparatus is thereby capable of use for Temporal Analysis of Products.

19. An apparatus as set forth in claim 18 wherein said mixing zone contains means for distributing said reactant gas radially with respect to the path of flow of gas through said zone.

20. An apparatus as set forth in claim 18 wherein said mixing zone contains means for randomizing the radial components of the flow vectors of the molecules of said reactant gas pulse.

21. An apparatus as set forth in claim 18 wherein the void volume of said mixing zone is not greater than about one tenth the volume of the reaction catalyst zone when the reaction catalyst zone is empty of catalyst.

* * * * *